(12) United States Patent
Snider et al.

(10) Patent No.: US 10,949,602 B2
(45) Date of Patent: Mar. 16, 2021

(54) SEQUENCING MEDICAL CODES METHODS AND APPARATUS

(71) Applicant: Nuance Communications, Inc., Burlington, MA (US)

(72) Inventors: Neal E. Snider, Belmont, MA (US); Feifan Liu, Shrewsbury, MA (US); Girija Yegnanarayanan, Raleigh, NC (US)

(73) Assignee: Nuance Communications, Inc., Burlington, MA (US)

(*) Notice: Subject to any disclaimer, the term of this patent is extended or adjusted under 35 U.S.C. 154(b) by 484 days.

(21) Appl. No.: 15/710,319

(22) Filed: Sep. 20, 2017

(65) Prior Publication Data
US 2018/0081859 A1    Mar. 22, 2018

Related U.S. Application Data

(60) Provisional application No. 62/397,252, filed on Sep. 20, 2016.

(51) Int. Cl.
*G06Q 50/22* (2018.01)
*G06F 40/10* (2020.01)
(Continued)

(52) U.S. Cl.
CPC .......... *G06F 40/10* (2020.01); *G06F 40/169* (2020.01); *G06F 40/20* (2020.01); *G06F 40/279* (2020.01);
(Continued)

(58) Field of Classification Search
CPC ........ G16H 10/60; G16H 15/00; G16H 40/20; G16H 50/20; G16H 50/70; G16H 40/63;
(Continued)

(56) References Cited

U.S. PATENT DOCUMENTS

| | | |
|---|---|---|
| 4,696,039 A | 9/1987 | Doddington |
| 5,031,113 A | 7/1991 | Hollerbauer |

(Continued)

FOREIGN PATENT DOCUMENTS

| | | |
|---|---|---|
| DE | 19533541 C1 | 3/1997 |
| DE | 102007021284 A1 | 11/2008 |

(Continued)

OTHER PUBLICATIONS

International Search Report and Written Opinion for International Application No. PCT/US2015/033642 dated Sep. 9, 2015.

(Continued)

*Primary Examiner* — Maroun P Kannan
(74) *Attorney, Agent, or Firm* — Wolf, Greenfield & Sacks, P.C.

(57) ABSTRACT

Some aspect include a system for automatically processing text comprising information regarding a patient encounter to prioritize medical billing codes derived from the text. The system comprises at least one storage medium storing processor-executable instructions, and at least one processor configured to execute the processor-executable instructions to analyze the text to extract a plurality of facts from the text, assign a plurality of medical billing codes to the text based at least in part on the plurality of facts, using a model trained at least in part on feedback from a user, order the plurality of medical billing codes in a sequence beginning with a primary medical billing code corresponding to a primary diagnosis associated with the text, and present the ordered sequence of medical billing codes to the user for review.

20 Claims, 26 Drawing Sheets

(51) Int. Cl.

| | | |
|---|---|---|
| *G16H 15/00* | (2018.01) | |
| *G06F 40/20* | (2020.01) | |
| *G06F 40/44* | (2020.01) | |
| *G06F 40/55* | (2020.01) | |
| *G06F 40/169* | (2020.01) | |
| *G06F 40/279* | (2020.01) | |
| *G10L 15/26* | (2006.01) | |
| *G06Q 50/24* | (2012.01) | |

(52) U.S. Cl.
CPC .............. *G06F 40/44* (2020.01); *G06F 40/55* (2020.01); *G06Q 50/24* (2013.01); *G10L 15/26* (2013.01); *G16H 15/00* (2018.01)

(58) Field of Classification Search
CPC ....... G16H 80/00; G06F 40/10; G06F 40/169; G06F 40/279; G06F 40/30; G06F 19/324; G06F 40/284; G06F 16/84; G06F 40/117; G06F 40/14; G06F 40/40; G06F 40/44
See application file for complete search history.

(56) References Cited

U.S. PATENT DOCUMENTS

| | | |
|---|---|---|
| 5,051,924 A | 9/1991 | Bergeron et al. |
| 5,307,262 A | 4/1994 | Ertel |
| 5,680,511 A | 10/1997 | Baker et al. |
| 5,758,322 A | 5/1998 | Rongley |
| 5,787,394 A | 7/1998 | Bahl et al. |
| 5,909,667 A | 6/1999 | Leontiades et al. |
| 5,924,074 A | 7/1999 | Evans |
| 5,999,896 A | 12/1999 | Richardson et al. |
| 6,003,002 A | 12/1999 | Netsch |
| 6,073,101 A | 6/2000 | Maes |
| 6,173,259 B1 | 1/2001 | Bijl et al. |
| 6,212,498 B1 | 4/2001 | Sherwood et al. |
| 6,292,771 B1 | 9/2001 | Haug et al. |
| 6,360,237 B1 | 3/2002 | Schulz et al. |
| 6,366,882 B1 | 4/2002 | Bijl et al. |
| 6,418,410 B1 | 7/2002 | Nassiff et al. |
| 6,434,547 B1 | 8/2002 | Mishelevich et al. |
| 6,463,413 B1 | 10/2002 | Applebaum et al. |
| 6,487,530 B1 | 11/2002 | Lin et al. |
| 6,519,561 B1 | 2/2003 | Farrell et al. |
| 6,567,778 B1 | 5/2003 | Chao Chang et al. |
| 6,813,603 B1 | 11/2004 | Groner et al. |
| 6,915,254 B1 | 7/2005 | Heinze et al. |
| 7,233,938 B2 | 6/2007 | Carus et al. |
| 7,383,172 B1 | 6/2008 | Jamieson |
| 7,493,253 B1 | 2/2009 | Ceusters et al. |
| 7,610,192 B1 | 10/2009 | Jamieson |
| 7,983,922 B2 | 7/2011 | Neusinger et al. |
| 8,204,756 B2 | 6/2012 | Kim et al. |
| 8,208,641 B2 | 6/2012 | Oh et al. |
| 8,326,653 B2 | 12/2012 | Gottlieb et al. |
| 8,612,261 B1 | 12/2013 | Swanson et al. |
| 8,694,335 B2 | 4/2014 | Yegnanarayanan |
| 8,756,079 B2 | 6/2014 | Yegnanarayanan |
| 8,943,437 B2 | 1/2015 | Meurs |
| 9,324,321 B2 | 4/2016 | Xue et al. |
| 9,478,218 B2 | 10/2016 | Shu |
| 9,715,576 B2 | 7/2017 | Hayter, II |
| 10,319,004 B2 | 6/2019 | Reiser et al. |
| 10,331,763 B2 | 6/2019 | Subramanian et al. |
| 10,366,424 B2 | 7/2019 | Spitznagel et al. |
| 10,366,687 B2 | 7/2019 | Zhan et al. |
| 10,373,711 B2 | 8/2019 | D'Souza et al. |
| 10,754,925 B2 | 8/2020 | D'Souza et al. |
| 2003/0115083 A1 | 6/2003 | Masarie, Jr. et al. |
| 2003/0163461 A1 | 8/2003 | Gudbjartsson et al. |
| 2003/0212544 A1 | 11/2003 | Acero et al. |
| 2004/0044952 A1 | 3/2004 | Jiang et al. |
| 2004/0073458 A1 | 4/2004 | Jensen |
| 2004/0220831 A1 | 11/2004 | Fabricant |
| 2005/0033574 A1 | 2/2005 | Kim et al. |
| 2005/0228815 A1 | 10/2005 | Carus et al. |
| 2005/0240439 A1 | 10/2005 | Covit et al. |
| 2006/0136197 A1 | 6/2006 | Oon |
| 2006/0190300 A1 | 8/2006 | Drucker et al. |
| 2006/0242190 A1 | 10/2006 | Wnek |
| 2007/0033026 A1 | 2/2007 | Bartosik et al. |
| 2007/0050187 A1 | 3/2007 | Cox |
| 2007/0088564 A1 | 4/2007 | March et al. |
| 2007/0208567 A1 | 9/2007 | Amento et al. |
| 2008/0002842 A1 | 1/2008 | Neusinger et al. |
| 2008/0004505 A1 | 1/2008 | Kapit et al. |
| 2008/0147436 A1 | 6/2008 | Ohlsson |
| 2008/0222734 A1 | 9/2008 | Redlich et al. |
| 2008/0255835 A1 | 10/2008 | Ollason et al. |
| 2008/0262853 A1 | 10/2008 | Jung et al. |
| 2008/0270120 A1 | 10/2008 | Pestian et al. |
| 2009/0157411 A1 | 6/2009 | Kim et al. |
| 2009/0210238 A1 | 8/2009 | Kim et al. |
| 2009/0216528 A1 | 8/2009 | Gemello et al. |
| 2009/0281839 A1 | 11/2009 | Lynn et al. |
| 2009/0326958 A1 | 12/2009 | Kim et al. |
| 2010/0023319 A1 | 1/2010 | Bikel et al. |
| 2010/0049756 A1 | 2/2010 | Chemitiganti et al. |
| 2010/0076772 A1 | 3/2010 | Kim et al. |
| 2010/0076774 A1 | 3/2010 | Breebaart |
| 2010/0161316 A1 | 6/2010 | Haug |
| 2010/0198602 A1 | 8/2010 | Oh et al. |
| 2010/0250236 A1 | 9/2010 | Jagannathan et al. |
| 2010/0274584 A1 | 10/2010 | Kim |
| 2011/0040576 A1 | 2/2011 | Madan et al. |
| 2012/0078763 A1 | 3/2012 | Koll et al. |
| 2012/0089629 A1 | 4/2012 | Koll et al. |
| 2012/0109641 A1 | 5/2012 | Boone et al. |
| 2012/0215559 A1 | 8/2012 | Flanagan et al. |
| 2012/0245961 A1 | 9/2012 | Yegnanarayanan |
| 2013/0035961 A1 | 2/2013 | Yegnanarayanan |
| 2013/0041685 A1* | 2/2013 | Yegnanarayanan .... G16H 50/20 705/2 |
| 2013/0067319 A1 | 3/2013 | Olszewski et al. |
| 2013/0073301 A1 | 3/2013 | Rao et al. |
| 2013/0080187 A1 | 3/2013 | Bacon et al. |
| 2013/0246098 A1 | 9/2013 | Habboush et al. |
| 2013/0297347 A1 | 11/2013 | Cardoza et al. |
| 2013/0297348 A1 | 11/2013 | Cardoza et al. |
| 2013/0318076 A1 | 11/2013 | Chiticariu et al. |
| 2014/0164023 A1 | 6/2014 | Yegnanarayanan |
| 2014/0244257 A1 | 8/2014 | Colibro et al. |
| 2014/0257803 A1 | 9/2014 | Yu et al. |
| 2014/0278460 A1 | 9/2014 | Dart et al. |
| 2014/0280353 A1 | 9/2014 | Delaney et al. |
| 2014/0343957 A1 | 11/2014 | Dejori |
| 2014/0372147 A1 | 12/2014 | White |
| 2014/0372216 A1 | 12/2014 | Nath et al. |
| 2015/0039299 A1 | 2/2015 | Weinstein et al. |
| 2015/0039301 A1 | 2/2015 | Senior et al. |
| 2015/0039344 A1* | 2/2015 | Kinney ................ G06F 19/328 705/3 |
| 2015/0046178 A1 | 2/2015 | Jindal |
| 2015/0066974 A1 | 3/2015 | Winn |
| 2015/0095016 A1 | 4/2015 | Karres et al. |
| 2015/0112680 A1 | 4/2015 | Lu |
| 2015/0134361 A1 | 5/2015 | Molenda |
| 2015/0149165 A1 | 5/2015 | Saon |
| 2015/0161522 A1 | 6/2015 | Saon et al. |
| 2015/0161995 A1 | 6/2015 | Sainath et al. |
| 2015/0356057 A1 | 12/2015 | Subramanian et al. |
| 2015/0356198 A1 | 12/2015 | D'Souza et al. |
| 2015/0356246 A1 | 12/2015 | D'Souza et al. |
| 2015/0356260 A1 | 12/2015 | D'Souza et al. |
| 2015/0356458 A1 | 12/2015 | Berengueres et al. |
| 2015/0356646 A1 | 12/2015 | Spitznagel et al. |
| 2015/0356647 A1 | 12/2015 | Reiser et al. |
| 2015/0371634 A1 | 12/2015 | Kim |
| 2015/0379241 A1 | 12/2015 | Furst et al. |
| 2016/0012186 A1 | 1/2016 | Zasowski et al. |
| 2016/0085743 A1 | 3/2016 | Haley |
| 2016/0260428 A1 | 9/2016 | Matsuda et al. |
| 2016/0300034 A1 | 10/2016 | Huddar et al. |
| 2016/0364532 A1 | 12/2016 | Honeycutt et al. |

(56) References Cited

U.S. PATENT DOCUMENTS

| | | |
|---|---|---|
| 2017/0039326 A1 | 2/2017 | Stankiewicz et al. |
| 2017/0061085 A1 | 3/2017 | Nossal et al. |
| 2017/0104785 A1 | 4/2017 | Stolfo et al. |
| 2017/0116373 A1 | 4/2017 | Ginsburg et al. |
| 2017/0169815 A1 | 6/2017 | Zhan et al. |
| 2017/0300635 A1 | 10/2017 | Ganesan et al. |
| 2017/0323060 A1 | 11/2017 | D'Souza et al. |
| 2017/0323061 A1 | 11/2017 | D'Souza et al. |
| 2018/0032678 A1 | 2/2018 | Dandala et al. |
| 2018/0032679 A1 | 2/2018 | Dandala et al. |
| 2018/0052961 A1 | 2/2018 | Shrivastava et al. |
| 2018/0089373 A1 | 3/2018 | Matsuguchi et al. |
| 2018/0090142 A1 | 3/2018 | Li et al. |
| 2018/0119137 A1 | 5/2018 | Matsuguchi et al. |
| 2018/0373844 A1 | 12/2018 | Ferrandez-Escamez et al. |
| 2019/0080450 A1 | 3/2019 | Arar et al. |
| 2019/0130073 A1 | 5/2019 | Sun et al. |
| 2019/0325859 A1 | 10/2019 | Zhan et al. |
| 2019/0385202 A1 | 12/2019 | Reiser et al. |
| 2020/0126130 A1 | 4/2020 | Spitznagel et al. |
| 2020/0126643 A1 | 4/2020 | D'Souza et al. |

FOREIGN PATENT DOCUMENTS

| | | |
|---|---|---|
| EP | 1 361 522 A2 | 11/2003 |
| WO | WO 98/19253 A1 | 5/1998 |
| WO | WO 2013/133891 A1 | 9/2013 |
| WO | WO 2015/084615 A1 | 6/2015 |

OTHER PUBLICATIONS

International Search Report and Written Opinion for International Application No. PCT/US2015/033130 dated Aug. 6, 2015.
International Search Report and Written Opinion for International Application No. PCT/US2015/033648 dated Aug. 11, 2015.
International Search Report and Written Opinion for International Application No. PCT/US2016/061326 dated Feb. 21, 2017.
International Preliminary Report on Patentability for International Application No. PCT/US2016/061326 dated Jun. 21, 2018.
International Preliminary Report on Patentability for International Application No. PCT/US2017/052542 dated Apr. 4, 2019.
[No Author Listed], Asthma specificity and tobacco use highlight ICD-10-CM respiratory changes. HCPro. JustCoding News. 2014. 4 pages.
[No Author Listed], Chronic lower respiratory diseases J40-J47. 2015 ICD-10-CM Diagnosis Codes. ICD10Data.com 2015. 6 pages.
[No Author Listed], Injury, poisoning and certain other consequences of external causes S00-T88. 2015 ICD-10-CM Diagnosis Codes. ICD10Data.com 2015. 35 pages.
Abrash et al., Connectionist Speaker Normalization and Adaptation. Proc. EUROSPEECH'95, 1995. 4 pages.
Cimiano et al., "Learning concept hierarchies from text with a guided hierarchical clustering algorithm," In C. Biernann and G. Paas (eds.), Proceedings of the ICML 2005 Workshop on Learning and Extending Lexical Ontologies with Machine Learning Methods, Bonn, Germany, (2005).
Fan et al., "PRISMATIC: Inducing Knowledge from a Large Scale Lexicalized Relation Resource," Proceedings of the NAACL HLT 2010 First International Workshop on Formalisms and Methodology for Learning by Reading, pp. 122-127, Los Angeles, California, Jun. 2010.
Ferrao et al., Clinical Coding Support Based on Structured Data Stored in Electronic Health Records. IEEE International Conference on Bioinformatics and Biomedicine Workshops. 2012. 790-7.
Florian et al., "A Statistical Model for Multilingual Entity Detection and Tracking," Proceedings of the Human Language Technologies Conference 2004 (HLT-NAACL'04), (2004).
Gemello et al., Linear hidden transformations for adaptation of hybrid ANN/HMM Models. Speech Communication. 2007;49:827-35.
Gomez-Perez et al., "An overview of methods and tools for ontology learning from texts," Knowledge Engineering Review 19:3 p. 187-212, 2004.
Omar, Fast Approximate I-Vector Estimation Using PCA. Proc. ICASSP. IEEE, 2015;4495-9.
Salton et al., "A Vector Space Model for Automatic Indexing," Communications of the ACM, vol. 18, No. 11, Nov. 1975.
Saon et al., Speaker Adaptation of Neural Network Acoustic Models Using I-Vectors. IEEE. 2013;55-9.
Senior et al., Improving DNN speaker independence with I-vector inputs. 2014 IEEE International Conference on Acoustics, Speech and Signal Processing (ICASSP), IEEE. 2014;225-9.
Welty et al., "Large Scale Relation Detection," Proceedings of the NAACL HLT 2010 First International Workshop on Formalisms and Methodology for Learning by Reading, pp. 24-33, Los Angeles, California, Jun. 2010.
U.S. Appl. No. 16/526,443, filed Jul. 30, 2019, Spitznagel et al.
International Search Report and Written Opinion for International Application No. PCT/US2017/052542 dated Dec. 14, 2017.
Aronow et al., Ad Hoc Classification of Radiology Reports. Journal of the American Medical Informatics Association. 1999;6(5):393-411.
Bateman et al., The Quest for The Last 5%: Interfaces for Correcting Real-Time Speech-Generated Subtitles. Interactive Posters. CHI 2000. 2 pages.
Birnbaum et al., Report: A Voice Password System for Access Security. AT&T Technical Journal. 1986. 7 pages.
Bisani et al., Automatic Editing in a Back-End Speech-to-Text System. Proceedings of ACL-08: HLT. 2008:114-20.
Heng-Hsou et al., An Event-Driven and Ontology-Based Approach for the Delivery and Information Extraction of E-mails. IEEE. 2000. 103-9.
Hewitt et al., Real-Time Speech-Generated Subtitles: Problems and Solutions. ISCA Archive. 6th International Conference on Spoken Language Processing (ICSLP 2000). 2000. 5 pages.
Mendonca et al., Extracting information on pneumonia in infants using natural language processing of radiology reports. Journal of Biomedical Informatics. 2005;38:314-21.
Naik, Speaker Verification: A Tutorial. IEEE Communications Magazine. 1990:42-8.
Newman et al., Speaker Verifcation Through Large Vocabulary Continuous Speech Recognition. Dragon Systems, Inc. 1996. 4 pages.
Rosenberg, Evaluation of an Automatic Speaker-Verification System Over Telephone Lines. Manuscript received Sep. 9, 1975. The Bell System Technical Journal. 1976;55(6):723-44.
Shvaiko et al., Ontology Matching OM-2008. Papers from the ISWC Workshop. 2008. 271 pages.
Sistrom et al., Managing Predefined Templated and Macros for a Departmental Speech Recognition System Using Common Software. Journal of Digital Imaging. 2001;14(3):131-41.
Soderland et al., Automated Classification of Encounter Notes in a Computer Based Medical Record. MEDINFO 1995 Proceedings. 1995 IMIA. 9 pages.
Sonntag et al., A Discourse and Dialogue Infrastructure for Industrial Dissemination. German Research Center for AI (DFKI). Proceeding IWSDS'10 Proceedings of the Second international conference on Spoken dialogue systems for ambient environments. 2010. 12 pages.
Sonntag et al., RadSpeech's Mobile Dialogue System for Radiologists. IUI'12. 2012. 2 pages.
Suhm, Multimodal Interactive Error Recovery for Non-Conversation Speech User Interfaces. Dissertation. 1998. 292 pages.
Taira et al., Automatic Structuring of Radiology Free-Text Reports. infoRAD. Radiology 2001;21:237-45.

* cited by examiner

| Patient Name | John Doe | Sex | M |
|---|---|---|---|
| Document Type | Discharge Summary | Creation Date | 01-18-2011 |

Problems  Medications  Allergies  Social History  Procedures  Vital Signs            Show All Chief complaint: Patient is presenting chest pain and shortness of breath.

Medical history: The patient is hypertensive. He is also obese.

Social history: He smokes one pack per day. Drinks occasionally.

⊟ Problems(4)

Add Fact

| Name | Status |
|---|---|
| × Unspecified Chest Pain | active |
| × Shortness of Breath | active |
| × Unspecified Essential Hypertension | history |
| × Obesity Unspecified | history |

⊟ Medications(1)

Add Fact

| Name | Status | Schedules |
|---|---|---|
| × | | None |

⊟ Allergies(0)

Add Fact

| Name | Type | Status |
|---|---|---|

[ Save ] [ Dictate ] [ Complete ] [ Cancel ]

Document List 710

- History & Physical
  - 6/13/2014
  - 6/15/2014
- Discharge Summary — 712
  - 6/18/2014
- Emergency Room Record
  - 6/13/2014
- Consultation
  - 6/16/2014
- Progress Notes
  - 6/17/2014
- Operative Report
  - 6/13/2014

Submit — 750

720

Discharge Summary 6/18/2014

HISTORY OF PRESENT ILLNESS/ HOSPTIAL COURSE:

The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. He was intubated and put into the — 722 ICU. The patient is doing well today. No acute symptoms. He denies any chest pain or shortness of breath. No fevers or chills.

730

Code List 740

| Diagnosis | Procedure | | |
|---|---|---|---|
| | ICD9 | Description | POA |
| ⊙ | 518.81 | Acute Respiratory Failure | |
| ○ | 287.5 | Thrombocytopenia NOS | |
| ○ | 338.4 | Chronic Pain Syndrome | |
| ○ | 571.5 | Cirrhosis of Liver w/o Alcohol | |
| ○ | 303.90 | Alcohol Dependence NEC/NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

732

700

Document List

- History & Physical
  - 6/13/2014
  - 6/15/2014
- Discharge Summary
  - 6/18/2014
- Emergency Room Record
  - 6/13/2014
- Consultation
  - 6/16/2014
- Progress Notes
  - 6/17/2014
- Operative Report
  - 6/13/2014

Submit

Discharge Summary 6/18/2014

HISTORY OF PRESENT ILLNESS/ HOSPITAL COURSE:

The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. He was intubated and out into the ICU. The (Linked to 518.81) today. No acute symptoms. He denies any chest pain or shortness of breath. No fevers or chills.

Code List

| Diagnosis | Procedure | | |
|---|---|---|---|
| | ICD9 | Description | POA |
| ✓ | 518.81 | Acute Respiratory Failure | |
| ○ | 287.5 | Thrombocytopenia NOS | |
| ○ | 338.4 | Chronic Pain Syndrome | |
| ○ | 571.5 | Cirrhosis of Liver w/o Alcohol | |
| ○ | 303.90 | Alcohol Dependence NEC/NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

Document List (710)
- History & Physical
  - 6/13/2014
  - 6/15/2014
- Discharge Summary — 712
  - 6/18/2014
- Emergency Room Record
  - 6/13/2014
- Consultation
  - 6/16/2014
- Progress Notes
  - 6/17/2014
- Operative Report
  - 6/13/2014

Submit — 750

Document view (720)

Discharge Summary 6/18/2014
DISCHARGE DIAGNOSES:
1. Acute hypercapnic respiratory failure.
2. Thrombocytopenia. — 726
3. Chronic pain syndrome.
4. History of liver cirrhosis.
5. Alcoholism.
6. Congestive heart failure (CHF)
7. History of multilobular pseudomonas pneumonia in sacral wounds with general deconditioning, weakness and fatigue.

HISTORY OF PRESENT ILLNESS/ HOSPITAL COURSE
The patient is a 63-year old male with a history of multiple medical problems. He was originally admitted on June 13 when he was found

Code List (730, 740)

| Diagnosis | Procedure | | |
|---|---|---|---|
| | ICD9 | Description | POA |
| ☑ | 518.81 | Acute Respiratory Failure | |
| ○ | 287.5 | Thrombocytopenia NOS | |
| ○ | 338.4 | Chronic Pain Syndrome | |
| ○ | 571.5 | Cirrhosis of Liver w/o Alcohol | |
| ○ | 303.90 | Alcohol Dependence NEC/NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

FIG. 7E

Document List (710):
- History & Physical
  - 6/13/2014
  - 6/15/2014
- Discharge Summary (712)
  - 6/18/2014
- Emergency Room Record
  - 6/16/2014
- Consultation
  - 6/16/2014
- Progress Notes
  - 6/17/2014
- Operative Report
  - 6/13/2014

Submit (750)

Document view (720):

Discharge Summary 6/18/2014
DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CHF)
7. History of multilobular pseudomonas pneumonia in sacral wounds with general deconditioning, weakness and fatigue.

HISTORY OF PRESENT ILLNESS/HOSPITAL COURSE
The patient is a 63-year old male with a history of multiple medical problems. He was originally admitted on June 13 when he was found Code List (730/740):

| Diagnosis | Procedure | | |
|---|---|---|---|
| ICD9 | Description | | PQA |
| 518.81 | Acute Respiratory Failure | ✓ | |
| 287.5 | Thrombocytopenia NOS | ✓ | |
| 338.4 | Chronic Pain Syndrome | ⊘ | (734) |
| 571.5 | Cirrhosis of Liver w/o Alcohol | ⊘ | (736) |
| 303.90 | Alcohol Dependence NEC/NOS | ✓ | |
| 571.2 | Alcoholic Cirrhosis of Liver | ✓ | |
| 428.0 | Congestive Heart Failure, Unspec | ✓ | (738) |
| 482.1 | Pneumonia due to Pseudomonas | ⊕ | |
| 041.7 | Pseudomonas Infection Site NOS | ⊕ | |

FIG. 7F

| Save | | | |
|---|---|---|---|
| | Code | Description | POA |
| 1. | 518.81 | Acute Respiratory Failure | N |
| 2. | 287.5 | Thrombocytopenia NOS | Y |
| 3. | 338.4 | Chronic Pain Syndrome | Y |
| 4. | 303.90 | Alcohol Dependence NEC/NOS | Y |
| 5. | 571.2 | Alcoholic Cirrhosis of Liver | Y |
| 6. | 428.0 | Congestive Heart Failure, Unspecified | Y |
| 7. | 482.1 | Pneumonia due to Pseudomonas | Y |
| 8. | 041.7 | Pseudomonas Infection Site NOS/Dis Class Elsewhere | Y |

FIG. 7G

Document List — 710

Submit — 750

- History & Physical
  - 6/13/2014
  - 6/15/2014
- Discharge Summary — 712
  - 6/18/2014
- Emergency Room Record
  - 6/13/2014
- Consultation
  - 6/16/2014
- Progress Notes
  - 6/17/2014
- Operative Report
  - 6/13/2014

---

720

Discharge Summary 6/18/2014

DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CHF)
7. History of multilobular pseudomonas pneumonia in sacral wounds with general deconditioning, weakness and fatigue.

HISTORY OF PRESENT ILLNESS/ HOSPITAL COURSE

The patient is a 63-year old male with a history of multiple medical problems. He was originally admitted on June 13 when he was found

---

700 / 760 / 740

DRG: 189
PULMONARY EDEMA
& RESPIRATORY FAILURE

Code List — 730

| | | ICD9 | Description | POA |
|---|---|---|---|---|
| ○▽ | | | | |
| 1 | ⊘ | 518.81 | Acute Respiratory Failure | N |
| 2 | ⊘ | 287.5 | Thrombocytopenia NOS | Y |
| 3 | ⊘ | 338.4 | Chronic Pain Syndrome | Y |
| 4 | ⊘ | 571.5 | Cirrhosis of Liver w/o Alcohol | Y |
| | ⊘ | 303.90 | Alcohol Dependence NEC/NOS | Y |
| 5 | ⊘ | 571.2 | Alcoholic Cirrhosis of Liver | Y |
| 6 | ⊕ | 428.0 | Congestive Heart Failure, Unspec | Y |
| 7 | ⊕ | 482.1 | Pneumonia due to Pseudomonas | Y |
| 8 | ⊕ | 041.7 | Pseudomonas Infection Site NOS | Y |

FIG. 9A

Document List — 710

- History & Physical
  - 6/13/2014
  - 6/15/2014
- Discharge Summary — 712
  - 6/18/2014
- Emergency Room Record
  - 6/13/2014
- Consultation
  - 6/16/2014
- Progress Notes
  - 6/17/2014
- Operative Report
  - 6/13/2014

Submit — 750

Discharge Summary 6/18/2014 — 720

DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CHF).
7. History of multilobular pseudomonas pneumonia in sacral wounds with general deconditioning, weakness and fatigue.

HISTORY OF PRESENT ILLNESS/ HOSPITAL COURSE

The patient is a 63-year old male with a history of multiple medical problems. He was originally admitted on June 13 when he was found

DRG: 193
SIMPLE PNEUMONIA & PLEURISY W MCC

Code List — 730

| | | ICD9 | Description | POA |
|---|---|---|---|---|
| | ○▽ | | | |
| 2 | ⊘ | 518.81 | Acute Respiratory Failure | N |
| 3 | ⊘ | 287.5 | Thrombocytopenia NOS | Y |
| 4 | ⊘ | 338.4 | Chronic Pain Syndrome | Y |
| 5 | ⊘ | 571.5 | Cirrhosis of Liver w/o Alcohol | Y |
| 6 | ⊘ | 303.90 | Alcohol Dependence NEC/NOS | Y |
| 7 | ⊘ | 571.2 | Alcoholic Cirrhosis of Liver | Y |
| 1 | ⊕ | 428.0 | Congestive Heart Failure, Unspec | Y |
| 8 | ⊕ | 482.1 | Pneumonia due to Pseudomonas | Y |
| | ⊕ | 041.7 | Pseudomonas Infection Site NOS | Y |

Tabs: Diagnosis | Procedure — 740

DRG: 195
SIMPLE PNEUMONIA & PLEURISY W/O CC/MCC

Code List

| | | ICD9 | Description | POA |
|---|---|---|---|---|
| | Diagnosis | Procedure | | |
| 2 | ○ | 518.81 | Acute Respiratory Failure | |
| 3 | ⊘ | 287.5 | Thrombocytopenia NOS | Y |
| 4 | ⊘ | 338.4 | Chronic Pain Syndrome | Y |
| 5 | ⊘ | 571.5 | Cirrhosis of Liver w/o Alcohol | Y |
| 6 | ⊘ | 303.90 | Alcohol Dependence NEC/NOS | Y |
| 1 | ⊕ | 571.2 | Alcoholic Cirrhosis of Liver | Y |
| 7 | ⊕ | 428.0 | Congestive Heart Failure, Unspec | Y |
| | ⊕ | 482.1 | Pneumonia due to Pseudomonas | Y |
| | ⊕ | 041.7 | Pseudomonas Infection Site NOS | Y |

Discharge Summary 6/18/2014

DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CHF).
7. History of multilobular pseudomonas pneumonia in sacral wounds with general deconditioning, weakness and fatigue.

HISTORY OF PRESENT ILLNESS/ HOSPITAL COURSE

The patient is a 63-year old male with a history of multiple medical problems. He was originally admitted on June 13 when he was found Submit Document List ☐ History & Physical
  📄 6/13/2014
  📄 6/15/2014
☐ Discharge Summary
  📄 6/18/2014
☐ Emergency Room Record
  📄 6/13/2014
☐ Consultation
  📄 6/16/2014
☐ Progress Notes
  📄 6/17/2014
☐ Operative Report
  📄 6/13/2014

FIG. 9C

SEQUENCING MEDICAL CODES METHODS AND APPARATUS

RELATED APPLICATIONS

This application claims priority under 35 U.S.C. § 119(e) to U.S. Provisional Patent Application Ser. No. 62/397,252 filed Sep. 20, 2016 and entitled "Sequencing Medical Codes Methods and Apparatus," which application is herein incorporated by reference in its entirety.

BACKGROUND

Medical documentation is an important process in the healthcare industry. Most healthcare institutions maintain a longitudinal medical record (e.g., spanning multiple observations or treatments over time) for each of their patients, documenting, for example, the patient's history, encounters with clinical staff within the institution, treatment received, and/or plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

Historically, each patient's medical record was maintained as a physical paper folder, often referred to as a "medical chart", or "chart". Each patient's chart would include a stack of paper reports, such as intake forms, history and immunization records, laboratory results and clinicians' notes. Following an encounter with the patient, such as an office visit, a hospital round or a surgical procedure, the clinician conducting the encounter would provide a narrative note about the encounter to be included in the patient's chart. Such a note could include, for example, a description of the reason(s) for the patient encounter, an account of any vital signs, test results and/or other clinical data collected during the encounter, one or more diagnoses determined by the clinician from the encounter, and a description of a plan for further treatment. Often, the clinician would verbally dictate the note into an audio recording device or a telephone giving access to such a recording device, to spare the clinician the time it would take to prepare the note in written form. Later, a medical transcriptionist would listen to the audio recording and transcribe it into a text document, which would be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's age, gender, medical history, etc. Electronic medical records can also be shared, accessed and updated by multiple different personnel from local and remote locations through suitable user interfaces and network connections, eliminating the need to retrieve and deliver paper files from a crowded file room.

Another modern trend in healthcare management is the importance of medical coding for documentation and billing purposes. In the medical coding process, documented information regarding a patient encounter, such as the patient's diagnoses and clinical procedures performed, is classified according to one or more standardized sets of codes for reporting to various entities such as payment providers (e.g., health insurance companies that reimburse clinicians for their services). In the United States, some such standardized code systems have been adopted by the federal government, which then maintains the code sets and recommends or mandates their use for billing under programs such as Medicare.

For example, the International Classification of Diseases (ICD) numerical coding standard, developed from a European standard by the World Health Organization (WHO), was adopted in the U.S. in version ICD-9-CM (Clinically Modified). It is mandated by the Health Insurance Portability and Accountability Act of 1996 (HIPAA) for use in coding patient diagnoses. The Centers for Disease Control (CDC), the National Center for Health Statistics (NCHS), and the Centers for Medicare and Medicaid Services (CMS) are the U.S. government agencies responsible for overseeing all changes and modifications to ICD-9-CM, and a new version ICD-10-CM is scheduled for adoption in 2015.

Another example of a standardized code system adopted by the U.S. government is the Current Procedural Terminology (CPT) code set, which classifies clinical procedures in five-character alphanumeric codes. The CPT code set is owned by the American Medical Association (AMA), and its use is mandated by CMS as part of the Healthcare Common Procedure Coding System (HCPCS). CPT forms HCPCS Level I, and HCPCS Level II adds codes for medical supplies, durable medical goods, non-physician healthcare services, and other healthcare services not represented in CPT. CMS maintains and distributes the HCPCS Level II codes with quarterly updates.

Conventionally, the coding of a patient encounter has been a manual process performed by a human professional, referred to as a "medical coder" or simply "coder," with expert training in medical terminology and documentation as well as the standardized code sets being used and the relevant regulations. The coder would read the available documentation from the patient encounter, such as the clinicians' narrative reports, laboratory and radiology test results, etc., and determine the appropriate codes to assign to the encounter. The coder might make use of a medical coding system, such as a software program running on suitable hardware, that would display the documents from the patient encounter for the coder to read, and allow the coder to manually input the appropriate codes into a set of fields for entry in the record. Once finalized, the set of codes entered for the patient encounter could then be sent to a payment provider, which would typically determine the level of reimbursement for the encounter according to the particular codes that were entered.

SUMMARY

Some embodiments include a system for automatically processing text comprising information regarding a patient encounter to prioritize medical billing codes derived from the text. The system comprises at least one storage medium storing processor-executable instructions, and at least one processor configured to execute the processor-executable instructions to analyze the text to extract a plurality of facts from the text, assign a plurality of medical billing codes to the text based at least in part on the plurality of facts, using a model trained at least in part on feedback from a user, order the plurality of medical billing codes in a sequence beginning with a primary medical billing code corresponding to a primary diagnosis associated with the text, and present the ordered sequence of medical billing codes to the user for review.

Some embodiments comprise at least one computer readable medium storing instructions that, when executed by at least one processor, perform a method for automatically processing text comprising information regarding a patient encounter to assign a sequence to medical billing codes derived from the text, the method comprising analyzing the text to extract a plurality of facts from the text, assigning a plurality of medical billing codes to the text based at least in part on the plurality of facts, using a model trained at least in part on feedback from a user, ordering the plurality of medical billing codes in a sequence beginning with a first medical billing code corresponding to a primary diagnosis associated with the text, and presenting the ordered sequence of medical billing codes to the user for review.

Some embodiments comprise a method for automatically processing text comprising information regarding a patient encounter to assign a sequence to medical billing codes derived from the text, the method comprising analyzing the text to extract a plurality of facts from the text, assigning a plurality of medical billing codes to the text based at least in part on the plurality of facts, using a model trained at least in part on feedback from a user, ordering the plurality of medical billing codes in a sequence beginning with a first medical billing code corresponding to a primary diagnosis associated with the text, and presenting the ordered sequence of medical billing codes to the user for review.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 3A and 3B are screenshots illustrating an exemplary display of medical facts in a user interface in accordance with some embodiments;

FIG. 4 is a screenshot illustrating an exemplary display of linkage between text and a medical fact in accordance with some embodiments;

FIG. 5 is a screenshot illustrating an exemplary interface for entering a medical fact in accordance with some embodiments;

FIGS. 7A-7F are screenshots illustrating an exemplary user interface for a computer-assisted coding (CAC) system in accordance with some embodiments;

FIG. 7G is a display of medical codes ordered in a sequence by a sequencing engine, in accordance with some embodiments;

FIGS. 9A-C illustrate interface functionality for interacting with suggested billing codes;

DETAILED DESCRIPTION

Figure 1:
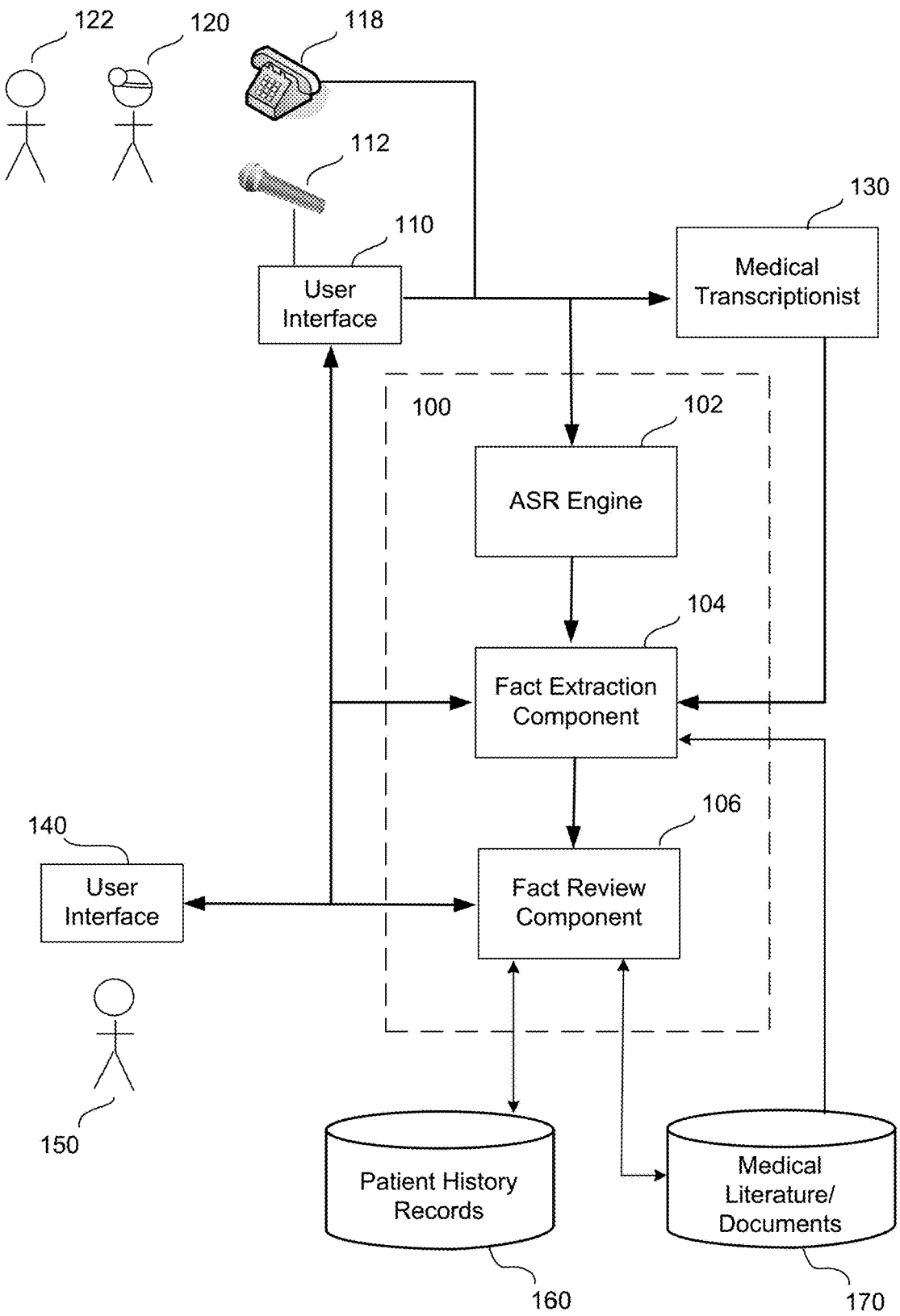
FIG. 1 is a block diagram of an exemplary operating environment for a clinical language understanding (CLU) system that may be employed in connection with some embodiments.

Medical codes are annotated in patient encounters in order to summarize and normalize the diagnoses made and procedures performed during the patient encounter. As part of the billing process for patent encounters, human medical coders sequence the codes by importance, with a primary diagnosis first, followed by one or more secondary diagnoses according to coding guidelines. Medical codes are also used for maintaining statistics on disorders and treatments and/or for various related research purposes so that sequencing of medical codes of patient encounters may follow institution-specific guidelines. Sequencing medical codes by importance or significance is an important part of a medical billing coder's job.

Computer-Assisted Medical Coding (CAC) systems have been designed to generate medical codes from documentation of a patient encounter, which are then reviewed, edited and sequenced manually by human coders. Manual editing of medical codes is time-consuming and tedious and can lead to mistakes in coding. The inventors have recognized and appreciated the benefit of automatically providing accurate medical code sequences corresponding to respective patient encounters to facilitate optimum reimbursement, reduce coding errors and/or increase productivity for medical billing coding specialists. The inventors have developed techniques to automatically learn code sequence ordering from training data according to coding standards as well as customer preferences, and to utilize customer feedback to further train the system to learn from customer's sequencing practices to adapt the system for particular users/customers.

Some embodiments are directed to a method comprising providing a plurality of medical billing codes generated for a free-form text documenting a clinical patient encounter to a sequencing engine configured to order the plurality of medical billing codes in a sequence beginning with a primary diagnosis followed by one or more secondary diagnoses ordered according to significance in the context of the corresponding clinical patient encounter. The sequence of medical billing codes for the clinical patient encounter generated by the sequencing engine may be presented to a user for billing, maintaining statistics on disorders and treatments and/or for related research. The user presented with the sequence of medical billing codes generated by the sequencing engine may make one or more corrections to the sequence of medical billing codes. The corrections can be used as feedback to adapt the sequencing engine to improve sequencing performance. Because the sequencing engine can be adapted based on specific user feedback, the sequencing engine can learn the behavior, practices and preferences of specific users, allowing the sequencing engine to be customized and/or configurable for each user. Some aspects relate to training such a sequencing engine.

Some embodiments described herein may make use of a natural language understanding (NLU) engine to automatically derive semantic information from free-form text and annotate the text with the derived information. One exemplary application of such techniques may be in automatically deriving and suggesting medical billing codes by applying the NLU engine to free-form text documenting a clinical patient encounter. Conventionally, ordering medical billing codes is performed manually, a process that is time intensive, tedious and prone to error. The inventors have recognized the benefit of automatically ordering medical codes in a sequence to assist medical coding specialists and facilitate more accurate and productive billing processes. Toward this end, the inventors have developed techniques that, based on medical codes determined for a patient encounter and features thereof, order the medical codes in a sequence for review by a human user (e.g., a medical billing coder).

According to some embodiments, free-form text documenting a clinical patient encounter may be provided to a NLU engine, which may be implemented via a processor. The NLU engine may analyze the text and generate annotations for appropriate portions of the text, as well as links between the annotations and their corresponding portions of the text, which together may constitute the engine annotations and links. The annotations may be medical codes representing medical diagnoses and/or medical procedures, as a non-limiting example, and in some embodiments may represent or be used as medical billing codes. Other types of annotations may additionally or alternatively be used. The annotations, including the medical codes and any other relevant features thereof (together referred to as "features") may be provided to a sequencing engine trained to order the medical codes in a sequenced based on significance or importance using the provided features. The medical code sequence may then be presented to a user or customer (e.g., a medical coding specialist), relieving the user/customer from much or all of the task of sequencing the medical codes for the patient encounter.

According to some embodiments, corrections to the medical billing codes, including re-ordering of the sequence and/or additions or deletions of medical codes are provided as feedback to improve the performance of the sequencing engine and/or the NLU engine. By adapting the system via user feedback, the system can learn customer specific preferences, practices and behaviors to customize the system accordingly.

The aspects and embodiments described above, as well as additional aspects and embodiments, are described further below. While a number of inventive features are described above and expanded upon below, it should be appreciated that embodiments of the present invention may include any one of these features, any combination of two or more features, or all of the features, as aspects of the invention are not limited to any particular number or combination of the above-described features. The aspects of the present invention described herein can be implemented in any of numerous ways, and are not limited to any particular implementation techniques. Described below are examples of specific implementation techniques; however, it should be appreciate that these examples are provided merely for purposes of illustration, and that other implementations are possible.

Clinical Language Understanding (CLU) System

An Electronic Health Record (EHR) is an electronic medical record that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as medical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack", "acute myocardial infarction", "acute MI" and "AMI". To facilitate interoperability of EHR data between various departments and users in the institution, and/or to allow identical conditions to be identified as such across patient records for data analysis, a typical EHR may use only one standardized term to represent each individual medical concept. For example, "acute myocardial infarction" may be the standard term stored in the EHR for every case of a heart attack occurring at the time of a clinical encounter. Some EHRs may represent medical terms in a data format corresponding to a coding standard, such as the International Classification of Disease (ICD) standard. For example, "acute myocardial infarction" may be represented in an EHR as "ICD-9 410", where 410 is the code number for "acute myocardial infarction" according to the ninth edition of the ICD standard.

To allow clinicians and other healthcare personnel to enter medical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

While some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete medical facts (e.g., clinical facts), such as could be stored as discrete structured data items in an electronic medical record, from a clinician's free-form narration of a patient encounter. In this manner, free-form input may be provided, but the advantages of storage, maintenance and accessing of medical documentation data in electronic forms may be maintained. For example, the storage of a patient's medical documentation data as a collection of discrete structured data items may provide the benefits of being able to query for individual data items of interest, and being able to assemble arbitrary subsets of the patient's data items into new reports, orders, invoices, etc., in an automated and efficient manner.

Automatic extraction of medical facts (e.g., clinical facts) from a free-form narration may be performed in any suitable way using any suitable technique(s), as aspects of the present invention are not limited in this respect. In some embodiments, pre-processing may be performed on a free-form narration prior to performing automatic fact extraction, to determine the sequence of words represented by the free-form narration. Such pre-processing may also be performed in any suitable way using any suitable technique(s), as aspects of the present invention are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the invention are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present invention are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present invention are not limited in this respect.

In some embodiments, one or more medical facts (e.g., clinical facts) may be automatically extracted from the free-form narration (in audio or textual form) or from a pre-processed data representation of the free-form narration using a fact extraction component applying natural language understanding techniques, such as a natural language understanding (NLU) engine. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. § 495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely exemplary, as aspects of the invention are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form, as aspects of the present invention are not limited in this respect. Exemplary implementations for a fact extraction component are described in detail below.

Some embodiments described herein may make use of a clinical language understanding (CLU) system, an exemplary operating environment for which is illustrated in FIG. 1. CLU system 100, illustrated in FIG. 1, may be implemented in any suitable form, as aspects of the present invention are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, exemplary system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104 and fact review component 106 may be implemented as a separate component of system 100, or any combination of these components may be integrated into a single component or a set of distributed components. In addition, any one of ASR engine 102, fact extraction component 104 and fact review component 106 may be implemented as a set of multiple software and/or hardware components. It should be understood that any such component depicted in FIG. 1 is not limited to any particular software and/or hardware implementation and/or configuration. Also, not all components of exemplary system 100 illustrated in FIG. 1 are required in all embodiments. For example, in some embodiments, a CLU system may include functionality of fact extraction component 104, which may be implemented using a natural language understanding (NLU) engine, without including ASR engine 102 and/or fact review component 106.

As illustrated in FIG. 1, user interface 110 is presented to a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, exemplary functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as aspects of the present invention are not limited in this respect.

Another way to provide a free-form narration of the patient encounter may be to verbally speak a dictation of the patient encounter. Such a spoken dictation may be provided in any suitable way, as aspects of the present invention are not limited in this respect. As illustrated in FIG. 1, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or any other suitable location (e.g., to a storage location accessible to system 100). Specifically, in some embodiments the text narrative may be received from medical transcriptionist 130 by fact extraction component 104 within system 100. Exemplary functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present invention are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semiautomatically by human editing of a draft transcription produced by ASR. Transcriptions produced by ASR engine 102 and/or by transcriptionist 130 may be encoded or otherwise represented as data in any suitable form, as aspects of the invention are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120. However, aspects of the invention are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104. However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as aspects of the invention are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

In some embodiments, either an original or a re-formatted text narrative may be received by fact extraction component 104, which may perform processing to extract one or more medical facts (e.g., clinical facts) from the text narrative. The text narrative may be received from ASR engine 102, from medical transcriptionist 130, directly from clinician 120 via user interface 110, or in any other suitable way. Any suitable technique(s) for extracting facts from the text narrative may be used, as aspects of the present invention are not limited in this respect. Exemplary techniques for medical fact extraction are described below.

In some embodiments, a fact extraction component may be implemented using techniques such as those described in U.S. Pat. No. 7,493,253, entitled "Conceptual World Representation Natural Language Understanding System and Method." U.S. Pat. No. 7,493,253 is incorporated herein by reference in its entirety. Such a fact extraction component may make use of a formal ontology linked to a lexicon of clinical terms. The formal ontology may be implemented as a relational database, or in any other suitable form, and may represent semantic concepts relevant to the medical domain, as well as linguistic concepts related to ways the semantic concepts may be expressed in natural language.

In some embodiments, concepts in a formal ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to the fact extraction component's formal ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the formal ontology. For example, the standard term "acute myocardial infarction" as well as other corresponding terms such as "heart attack", "acute MI" and "AMI" may all be linked to the same abstract concept in the formal ontology—a concept representing an interruption of blood supply to the heart. Such linkage of multiple medical terms to the same abstract concept in some embodiments may relieve the clinician of the burden of ensuring that only standard medical terms preferred by the institution appear in the free-form narration.

For example, in some embodiments, a clinician may be free to use the abbreviation "AMI" or the colloquial "heart attack" in his free-form narration, and the shared concept linkage may allow the fact extraction component to nevertheless automatically extract a fact corresponding to "acute myocardial infarction".

In some embodiments, a formal ontology used by a fact extraction component may also represent various types of relationships between the concepts represented. One type of relationship between two concepts may be a parent-child relationship, in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." In some embodiments, any other type(s) of relationship useful to the process of medical documentation may also be represented in the formal ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such a formal ontology, as aspects of the present invention are not limited in this respect.

In some embodiments, automatic extraction of medical facts from a clinician's free-form narration may involve parsing the free-form narration to identify medical terms that are represented in the lexicon of the fact extraction component. Concepts in the formal ontology linked to the medical terms that appear in the free-form narration may then be identified, and concept relationships in the formal ontology may be traced to identify further relevant concepts. Through these relationships, as well as the linguistic knowledge represented in the formal ontology, one or more medical facts may be extracted. For example, if the free-form narration includes the medical term "hypertension" and the linguistic context relates to the patient's past, the fact extraction component may automatically extract a fact indicating that the patient has a history of hypertension. On the other hand, if the free-form narration includes the medical term "hypertension" in a sentence about the patient's mother, the fact extraction component may automatically extract a fact indicating that the patient has a family history of hypertension. In some embodiments, relationships between concepts in the formal ontology may also allow the fact extraction component to automatically extract facts containing medical terms that were not explicitly included in the free-form narration. For example, the medical term "meningitis" can also be described as inflammation in the brain. If the free-form narration includes the terms "inflammation" and "brain" in proximity to each other, then relationships in the formal ontology between concepts linked to the terms "inflammation", "brain" and "meningitis" may allow the fact extraction component to automatically extract a fact corresponding to "meningitis", despite the fact that the term "meningitis" was not stated in the free-form narration.

It should be appreciated that the foregoing descriptions are provided by way of example only, and that any suitable technique(s) for extracting a set of one or more medical facts from a free-form narration may be used, as aspects of the present invention are not limited to any particular fact extraction technique. For instance, it should be appreciated that fact extraction component 104 is not limited to the use of an ontology, as other forms of knowledge representation models, including statistical models and/or rule-based models, may also be used. The knowledge representation model may also be represented as data in any suitable format, and may be stored in any suitable location, such as in a storage medium of system 100 accessible by fact extraction component 104, as aspects of the invention are not limited in this respect. In addition, a knowledge representation model such as an ontology used by fact extraction component 104 may be constructed in any suitable way, as aspects of the invention are not limited in this respect.

For instance, in some embodiments a knowledge representation model may be constructed manually by one or more human developers with access to expert knowledge about medical facts, diagnoses, problems, potential complications, comorbidities, appropriate observations and/or clinical findings, and/or any other relevant information. In other embodiments, a knowledge representation model may be generated automatically, for example through statistical analysis of past medical reports documenting patient encounters, of medical literature and/or of other medical documents. Thus, in some embodiments, fact extraction component 104 may have access to a data set 170 of medical literature and/or other documents such as past patient encounter reports. In some embodiments, past reports and/or other text documents may be marked up (e.g., by a human) with labels indicating the nature of the relevance of particular statements in the text to the patient encounter or medical topic to which the text relates. A statistical knowledge representation model may then be trained to form associations based on the prevalence of particular labels corresponding to similar text within an aggregate set of multiple marked up documents. For example, if "pneumothorax" is labeled as a "complication" in a large enough proportion of clinical procedure reports documenting pacemaker implantation procedures, a statistical knowledge representation model may generate and store a concept relationship that "pneumothorax is-complication-of pacemaker implantation." In some embodiments, automatically generated and hard coded (e.g., by a human developer) concepts and/or relationships may both be included in a knowledge representation model used by fact extraction component 104.

As discussed above, it should be appreciated that aspects of the invention are not limited to any particular technique(s) for constructing knowledge representation models. Examples of suitable techniques include those disclosed in the following:

Gómez-Pérez, A., and Manzano-Macho, D. (2005). *An overview of methods and tools for ontology learning from texts.* Knowledge Engineering Review 19, p. 187-212.

Cimiano, P., and Staab, S. (2005). *Learning concept hierarchies from text with a guided hierarchical clustering algorithm.* In C. Biemann and G. Paas (eds.), Proceedings of the ICML 2005 Workshop on Learning and Extending Lexical Ontologies with Machine Learning Methods, Bonn, Germany.

Fan, J., Ferrucci, D., Gondek, D., and Kalyanpur, A. (2010). *PRISMATIC: Inducing Knowledge from a Large Scale Lexicalized Relation Resource.* NAACL Workshop on Formalisms and Methodology for Learning by Reading.

Welty, C., Fan, J., Gondek, D. and Schlaikjer, A. (2010). *Large scale relation detection.* NAACL Workshop on Formalisms and Methodology for Learning by Reading.

Each of the foregoing publications is incorporated herein by reference in its entirety.

Alternatively or additionally, in some embodiments a fact extraction component may make use of one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input. Exemplary implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL'04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as aspects of the invention are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, e.g., in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as aspects of the invention are not limited in this respect.

In some embodiments, section membership may be used as a feature of a token. In some embodiments, a section normalization module may be implemented to associate various portions of the narrative text with the proper section to which it should belong. In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, discharge summaries, and emergency room reports, although there are also many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as aspects of the invention are not limited in this respect.

A section normalization module may use any suitable technique to associate portions of text with normalized document sections, as aspects of the invention are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N−1) words and/or tokens in the text as a feature of the current token. In another example, affixes (e.g., suffixes such as -ectomy, -oma, -itis, etc.) may be used as features of tokens. In another example, one or more predefined dictionaries and/or ontologies may be accessed, and a token's membership in any of those dictionaries may be used as a feature of that token. For example, a predefined dictionary of surgical procedures may be accessed, and/or a dictionary of body sites, and/or a dictionary of known diseases, etc. It should be appreciated, however, that all of the foregoing feature types are merely examples, and any suitable number and/or types of features of interest may be designated, e.g., by a developer of the statistical entity detection model, as aspects of the invention are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one exemplary implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely exemplary, as any suitable features may be used. Aspects of the invention are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as aspects of the invention are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability p1 that a token with that feature should be labeled as being part of a "Problem" entity, a probability p2 that a token with that feature should be labeled as being part of a "Medication" entity, etc. In some embodiments, such probabilities may be learned by determining the frequency with which tokens having the "-itis" feature were hand-labeled with each different entity label in the training corpus. In some embodiments, the probabilities may be normalized such that, for each feature, the probabilities of being associated with each possible entity (fact type) may sum to 1. However, aspects of the invention are not limited to such normalization. In some embodiments, each feature may also have a probability p0 of not being associated with any fact type, such that the non-entity probability p0 plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1−p1) of not being part of a "Problem" entity, probability p2 of being part of a "Medication" entity and probability (1−p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$ of its token being at the beginning of a "Problem" entity label, a probability $p_I$ of its token being inside a "Problem" entity label (but not at the beginning of the label), and a probability $p_O$ of its token being outside a "Problem" entity label (i.e., of its token not being part of a "Problem" entity).

In some embodiments, the statistical entity detection model may be further trained to weight the individual features of a token to determine an overall probability that it should be associated with a particular entity label. For example, if the token "sinusitis" has n extracted features f1 . . . fn having respective probabilities p1 . . . pn of being associated with a "Problem" entity label, the statistical model may be trained to apply respective weights w1 . . . wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as aspects of the invention are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as aspects of the invention are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N−1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions. In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in the sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as aspects of the invention are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that it is chronic and not, e.g., acute. Another exemplary type of relation may be an "attribute" relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. It should be appreciated, however, that the foregoing are merely examples, and that aspects of the invention are not limited to any particular attributes for any particular fact types. Also, other types of fact relations are possible, including family relative relations, causes-problem relations, improves-problem relations, and many others. Aspects of the invention are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as aspects of the invention are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely exemplary, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Exemplary techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as aspects of the invention are not limited in this respect. Some standard terms and/or codes may be derived from a government or profession-wide standard, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473. Any suitable coding system may be used, as aspects of the invention are not limited in this respect. Exemplary standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Exemplary techniques that may be used in some embodiments are described in Salton, Wong, & Yang: "A vector space model for automatic indexing," *Communications of the ACM*, November 1975. This publication is incorporated herein by reference in its entirety. However, these are merely examples, and any suitable technique(s) for normalizing entity tokens to standard terms may be utilized in some embodiments, as aspects of the invention are not limited in this respect.

In some embodiments, the normalization/coding process may output a single hypothesis for the standard form and/or code corresponding to each extracted fact. For example, the single output hypothesis may correspond to the concept linked in the ontology to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

It should be appreciated that the foregoing are merely examples, and that fact extraction component 104 may be implemented in any suitable way and/or form, as aspects of the invention are not limited in this respect.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One exemplary implementation of such a user interface is graphical user interface (GUI) 200, illustrated in FIG. 2. In some embodiments, when the user is clinician 120, GUI 200 may be presented via user interface 110. In some embodiments, a user may be a person other than a clinician; for example, another person such as coding specialist 150 may be presented with GUI 200 via user interface 140. However, it should be appreciated that "user," as used herein, refers to an end user of system 100, as opposed to a software and/or hardware developer of any component of system 100.

The user interface is not limited to a graphical user interface, as other ways of providing data from system 100 to users may be used. For example, in some embodiments, audio indicators may be transmitted from system 100 and conveyed to a user. It should be appreciated that any type of user interface may be provided in connection with fact extraction, fact review and/or other related processes, as aspects of the invention are not limited in this respect. While the exemplary embodiments illustrated in FIG. 1 involve data processing at system 100 and data communication between system 100 and user interfaces 110 and/or 140, it should be appreciated that in other embodiments any or all processing components of system 100 may instead be implemented locally at user interface 110 and/or user interface 140, as aspects of the invention are not limited to any particular distribution of local and/or remote processing capabilities.

Figure 2:
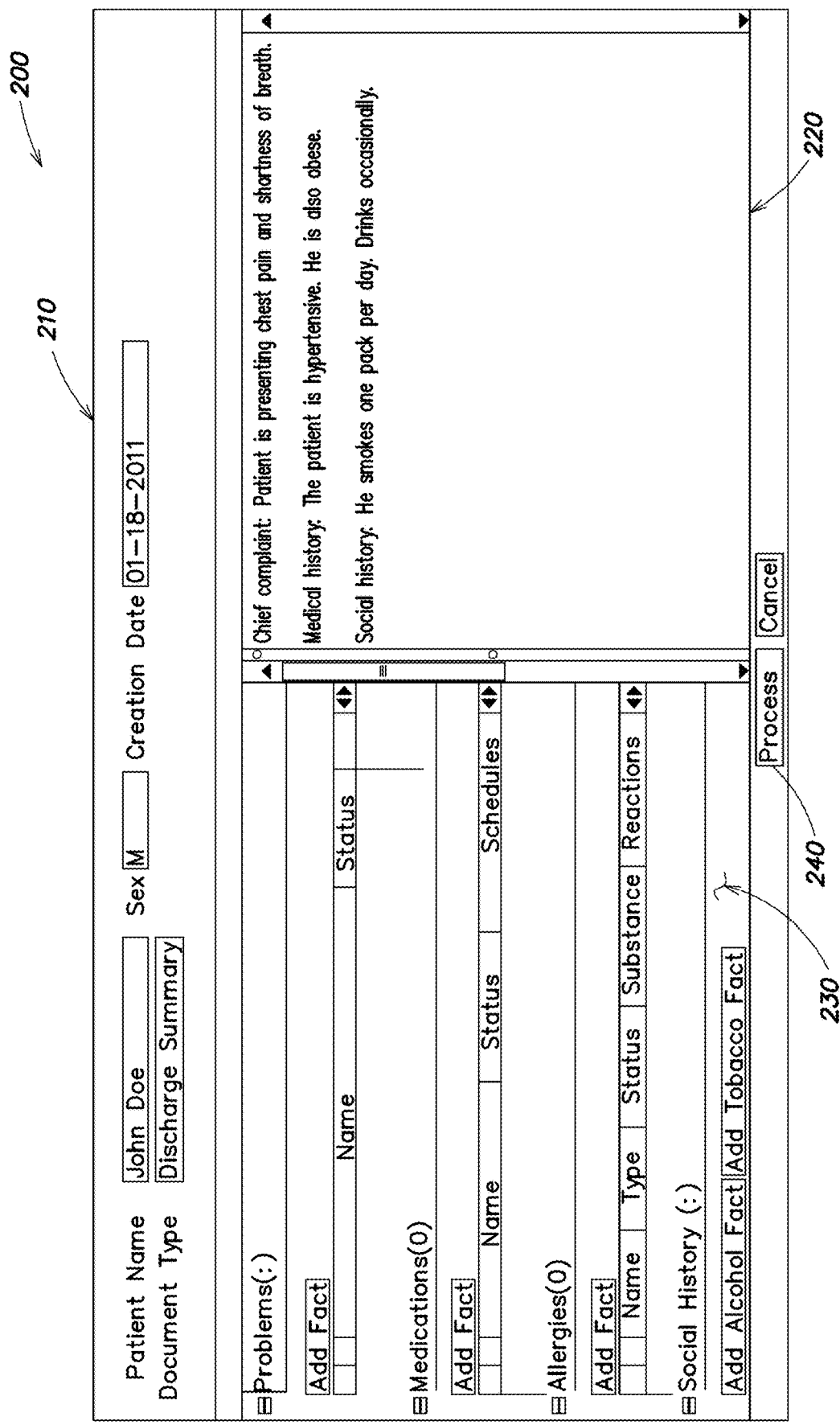
FIG. 2 is a screenshot illustrating an exemplary graphical user interface for review of extracted facts in accordance with some embodiments.

As depicted in FIG. 2, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touchscreen, stylus, voice, or any other suitable input form, as aspects of the invention are not limited in this respect.

GUI 200 as depicted in FIG. 2 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Exemplary GUI 200 further includes a fact panel 230 in which one or more medical facts, once extracted from the text narrative and/or entered in another suitable way, may be displayed as discrete structured data items. When clinician 120 and/or other user 150 is ready to direct fact extraction component 104 to extract one or more medical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and fact extraction component 104 may begin a fact extraction process as soon as a requisite amount of text (e.g., enough text for fact extraction component 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 3A:
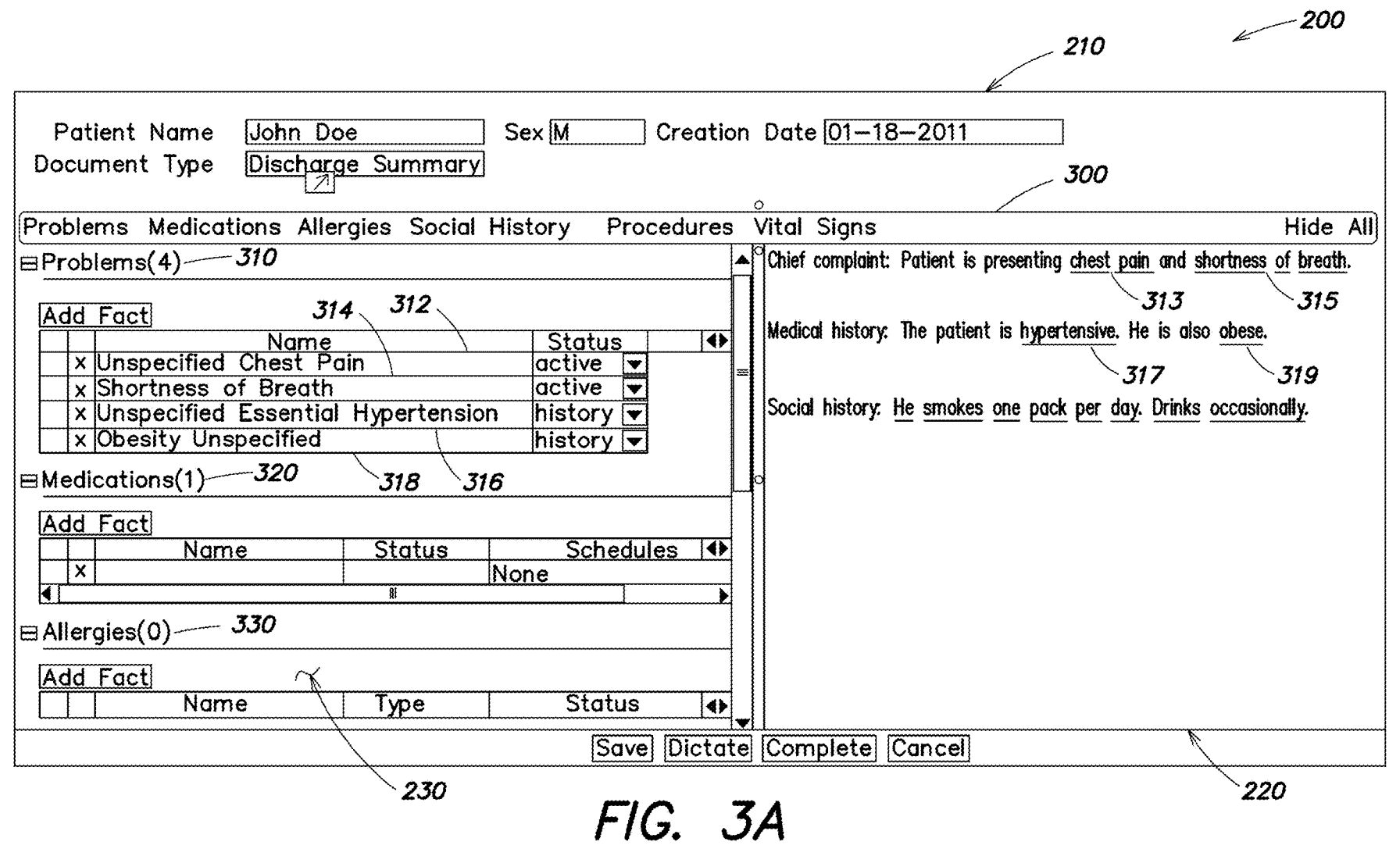
Figure 3B:
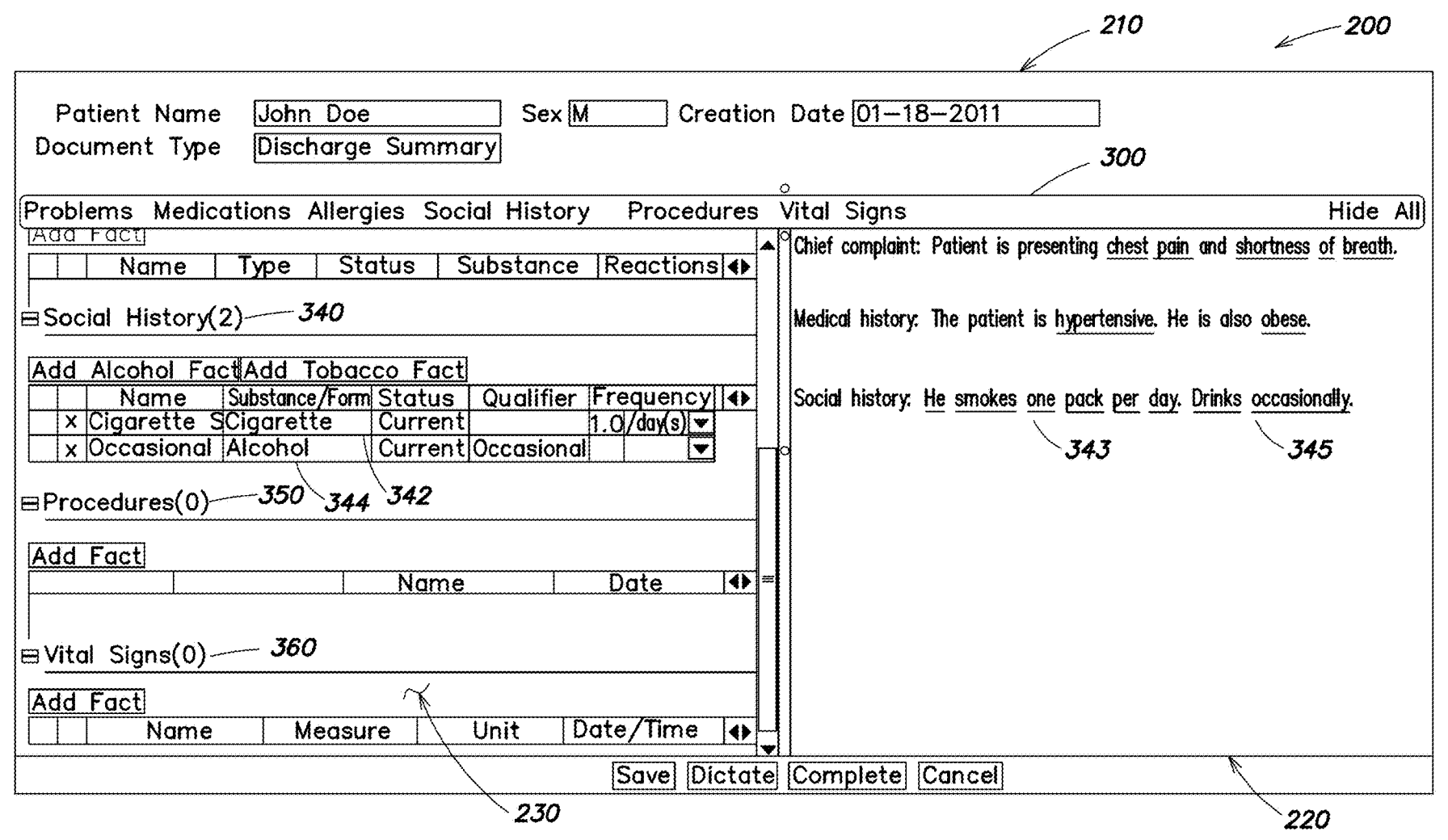

In some embodiments, one or more medical facts extracted from the text narrative by fact extraction component 104 may be displayed to the user via GUI 200 in fact panel 230. Screenshots illustrating an example display of medical facts extracted from an example text narrative are provided in FIGS. 3A and 3B. FIG. 3A is a screenshot with fact panel 230 scrolled to the top of a display listing medical facts extracted from the example text narrative, and FIG. 3B is a screenshot with fact panel 230 scrolled to the bottom of the display listing the extracted medical facts. In some embodiments, as depicted in FIGS. 3A and 3B, medical facts corresponding to a patient encounter may be displayed in fact panel 230, and organized into a number of separate categories of types of facts. An exemplary set of medical fact categories includes categories for problems, medications, allergies, social history, procedures and vital signs. However, it should be appreciated that any suitable fact categories may be used, as aspects of the invention are not limited in this respect. In addition, organization of facts into categories is not required, and displays without such organization are possible. As depicted in FIGS. 3A and 3B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. As depicted in FIGS. 3A and 3B, all available fact categories for the current document type are displayed, even if a particular fact category includes no extracted or otherwise entered medical facts. However, this is not required; in some embodiments, only those fact categories having facts ascertained from the patient encounter may be displayed in fact panel 230.

Fact panel 230 scrolled to the top of the display as depicted in FIG. 3A shows problem fact category 310, medications fact category 320, and allergies fact category 330. Within problem fact category 310, four clinical facts have been extracted from the example text narrative; no clinical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active". Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 3A, each clinical fact in problem fact category 310 has a name field and a status field. In some embodiments, each field of a clinical fact may be a structured component of that fact represented as a discrete structured data item. In this example, the name field may be structured such that only a standard set of medical terms for problems may be available to populate that field. For example, the status field may be structured such that only statuses in the Systematized Nomenclature of Medicine (SNOMED) standard (e.g., "active" and "history") may be selected within that field, although other standards (or no standard) could be employed. An exemplary list of fact categories and their component fields is given below. However, it should be appreciated that this list is provided by way of example only, as aspects of the invention are not limited to any particular organizational system for facts, fact categories and/or fact components.

Exemplary list of fact categories and component fields:
Category: Problems. Fields: Name, SNOMED status, ICD code.
Category: Medications. Fields: Name, Status, Dose form, Frequency, Measures, RxNorm code, Administration condition, Application duration, Dose route.
Category: Allergies. Fields: Allergen name, Type, Status, SNOMED code, Allergic reaction, Allergen RxNorm.
Category: Social history—Tobacco use. Fields: Name, Substance, Form, Status, Qualifier, Frequency, Duration, Quantity, Unit type, Duration measure, Occurrence, SNOMED code, Norm value, Value.
Category: Social history—Alcohol use. Fields: Name, Substance, Form, Status, Qualifier, Frequency, Duration, Quantity, Quantifier, Unit type, Duration measure, Occurrence, SNOMED code, Norm value, Value.
Category: Procedures. Fields: Name, Date, SNOMED code.
Category: Vital signs. Fields: Name, Measure, Unit, Unit type, Date/Time, SNOMED code, Norm value, Value.

In some embodiments, a linkage may be maintained between one or more medical facts extracted by fact extraction component 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 312 indicating that patient 122 is currently presenting with unspecified chest pain may have been extracted by fact extraction component 104 from the words "chest pain" in the text narrative. The "active" status of extracted fact 312 may have been determined by fact extraction component 104 based on the appearance of the words "chest pain" in the section of the text narrative with the section heading "Chief complaint". In some embodiments, fact extraction component 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 3A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Aspects of the invention are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by fact extraction component 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as aspects of the invention are not limited in this respect.

Fact panel 230 scrolled to the bottom of the display as depicted in FIG. 3B shows social history fact category 340, procedures fact category 350, and vital signs fact category 360. Within social history fact category 340, two clinical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

In some embodiments, GUI 200 may be configured to allow the user to select one or more of the medical facts in fact panel 230, and in response to the selection, to provide an indication of the portion(s) of the text narrative from which those fact(s) were extracted. An example is illustrated in FIG. 4. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as aspects of the invention are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as aspects of the invention are not limited in this respect. In addition, aspects of the invention are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain". In other embodiments, the audio indicator may be provided by playing an audio version of the words "chest pain" generated using automatic speech synthesis. Any suitable form of indicator or technique for providing indicators may be used, as aspects of the invention are not limited in this respect.

In some embodiments, GUI 200 may be configured to provide any of various ways for the user to make one or more changes to the set of medical facts extracted from the text narrative by fact extraction component 104 and displayed in fact panel 230, and these changes may be collected by fact review component 106 and applied to the documentation of the patient encounter. For example, the user may be allowed to delete a fact from the set in fact panel 230, e.g., by selecting the "X" option appearing next to the fact. In some embodiments, the user may be allowed to edit a fact within fact panel 230. In one example, the user may edit the name field of fact 312 by selecting the fact and typing, speaking or otherwise providing a different name for that fact. As depicted in FIG. 3A and FIG. 4, in some embodiments the user may edit the status field of fact 312 by selecting a different status from the available drop-down menu, although other techniques for allowing editing of the status field are possible. In some embodiments, the user may alternatively or additionally be allowed to edit a fact by interacting with the text narrative in text panel 220. For example, the user may add, delete, or change one or more words in the text narrative, and then the text narrative may be re-processed by fact extraction component 104 to extract an updated set of medical facts. In some embodiments, the user may be allowed to select only a part of the text narrative in text panel 220 (e.g., by highlighting it), and have fact extraction component 104 re-extract facts only from that part, without disturbing facts already extracted from other parts of the text narrative.

Figure 5:
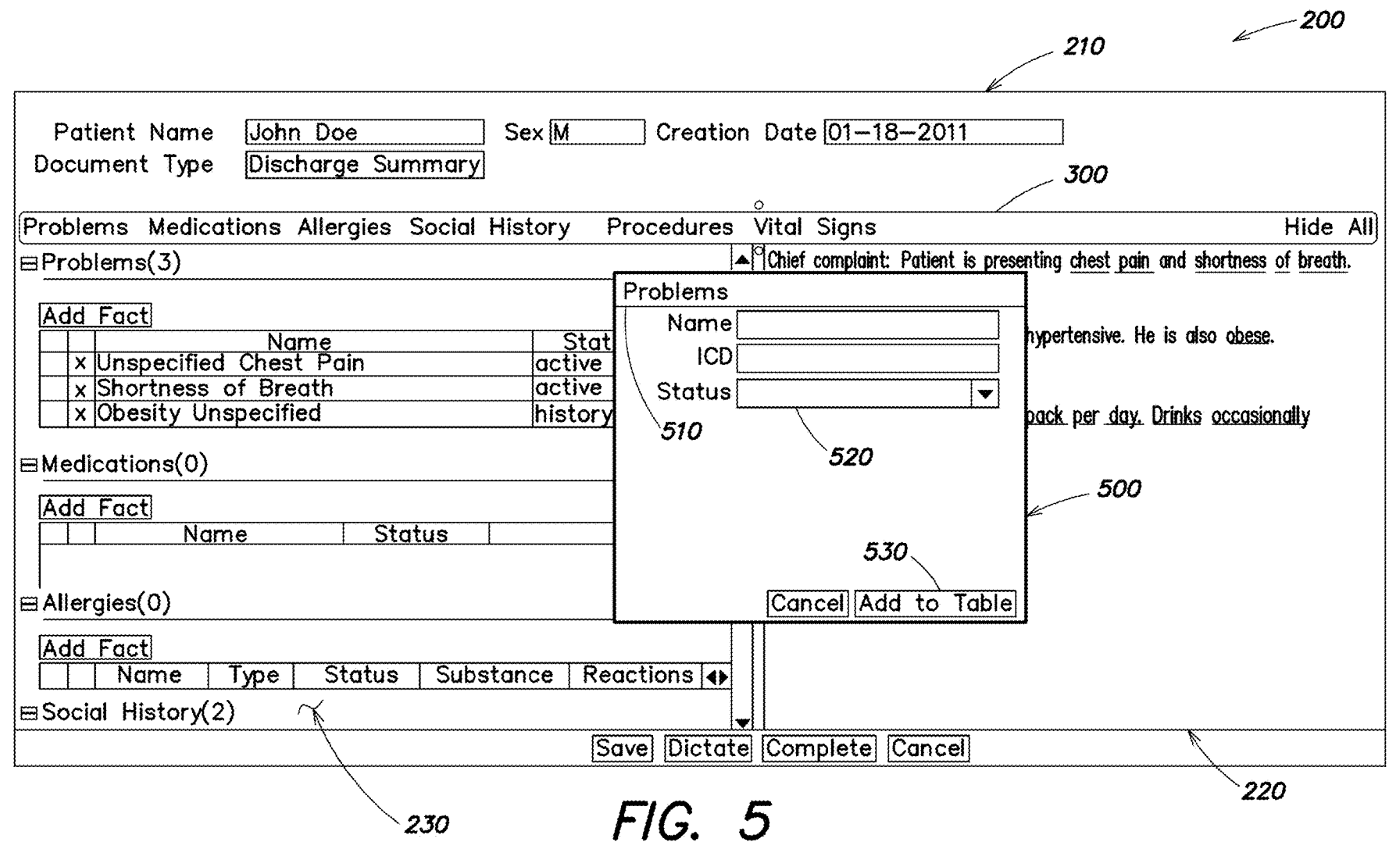

In some embodiments, GUI 200 may be configured to provide any of various ways for one or more facts to be added as discrete structured data items. As depicted in FIG. 4, GUI 200 in some embodiments may be configured to provide an add fact button for each fact category appearing in fact panel 230; one such add fact button is add fact button 430. When the user selects add fact button 430, in some embodiments GUI 200 may provide the user with a way to enter information sufficient to populate one or more fields of a new fact in that fact category, for example by displaying pop-up window 500 as depicted in FIG. 5. It should be appreciated that this is merely one example, as aspects of the invention are not limited to the use of pop-up windows or any other particular method for adding a fact. In this example, pop-up window 500 includes a title bar 510 that indicates the fact category ("Problems") to which the new fact will be added. Pop-up window 500 also provides a number of fields 520 in which the user may enter information to define the new fact to be added. Fields 520 may be implemented in any suitable form, including as text entry boxes, drop-down menus, radio buttons and/or checkboxes, as aspects of the invention are not limited to any particular way of receiving input defining a fact. Finally, pop-up window 500 includes add button 530, which the user may select to add the newly defined fact to the set of facts corresponding to the patient encounter, thus entering the fact as a discrete structured data item.

In some embodiments, GUI 200 may alternatively or additionally be configured to allow the user to add a new fact by selecting a (not necessarily contiguous) portion of the text narrative in text panel 220, and indicating that a new fact should be added based on that portion of the text narrative. This may be done in any suitable way. In one example, the user may highlight the desired portion of the text narrative in text panel 220, and right-click on it with a mouse (or perform another suitable input operation), which may cause the designated text to be processed and any relevant facts to be extracted. In other embodiments, the right-click or other input operation may cause a menu to appear. In some embodiments the menu may include options to add the new fact under any of the available fact categories, and the user may select one of the options to indicate which fact category will correspond to the new fact. In some embodiments, an input screen such as pop-up window 500 may then be provided, and the name field may be populated with the words selected by the user from the text narrative. The user may then have the option to further define the fact through one or more of the other available fields, and to add the fact to the set of medical facts for the patient encounter as described above.

In some embodiments, the set of medical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. In some embodiments, clinician 120 and/or coding specialist (or other user) 150 may finally approve the set of medical facts before they are included in any patient record; however, aspects of the present invention are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

Figure 6:
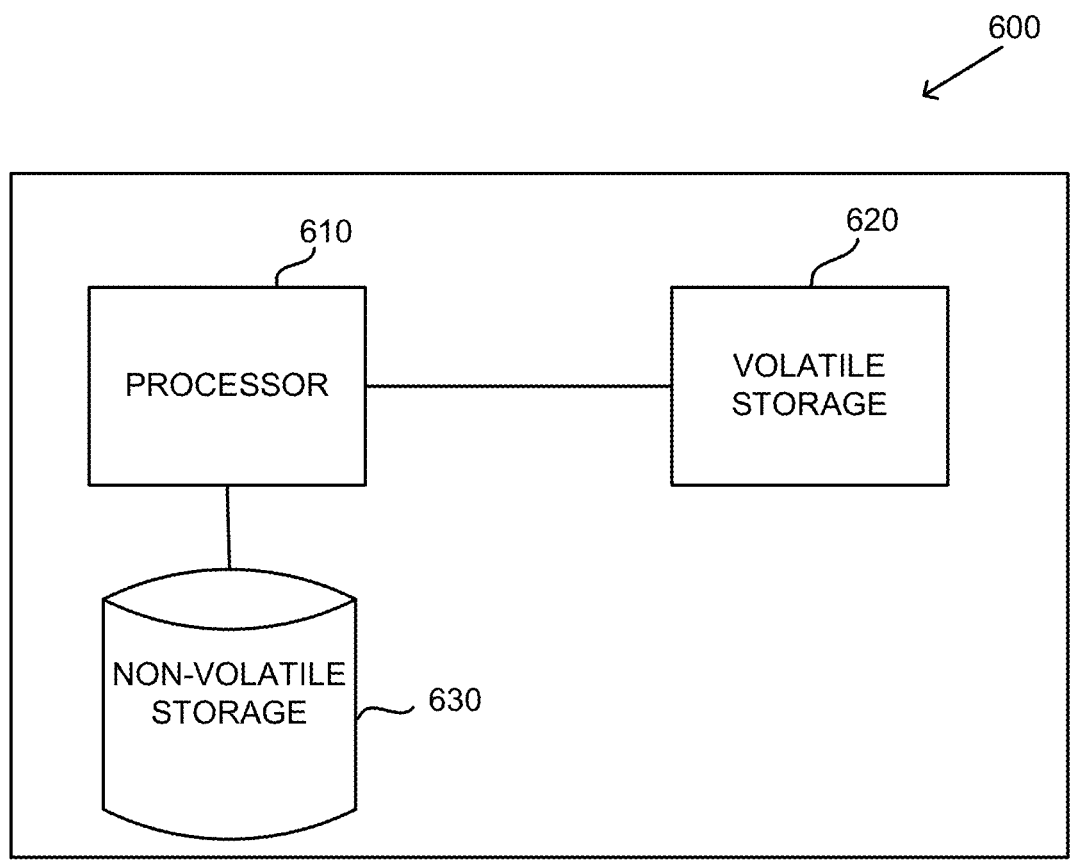
FIG. 6 is a block diagram of an exemplary computer system on which aspects of some embodiments may be implemented.

A CLU system in accordance with the techniques described herein may take any suitable form, as aspects of the present invention are not limited in this respect. An illustrative implementation of a computer system 600 that may be used in connection with some embodiments of the present invention is shown in FIG. 6. One or more computer systems such as computer system 600 may be used to implement any of the functionality described above. The computer system 600 may include one or more processors 610 and one or more tangible, non-transitory computer-readable storage media (e.g., volatile storage 620 and one or more non-volatile storage media 630, which may be formed of any suitable non-volatile data storage media). The processor 610 may control writing data to and reading data from the volatile storage 620 and the non-volatile storage device 630 in any suitable manner, as the aspects of the present invention are not limited in this respect. To perform any of the functionality described herein, the processor 610 may execute one or more instructions stored in one or more computer-readable storage media (e.g., volatile storage 620), which may serve as tangible, non-transitory computer-readable storage media storing instructions for execution by the processor 610.

Computer-Assisted Coding (CAC) System

As discussed above, medical coding for billing has conventionally been a manual process whereby a human professional (the "coder") reads all of the documentation for a patient encounter and enters the appropriate standardized codes (e.g., ICD codes, HCPCS codes, etc.) corresponding to the patient's diagnoses, procedures, etc. The coder is often required to understand and interpret the language of the clinical documents in order to identify the relevant diagnoses, etc., and assign them their corresponding codes, as the language used in clinical documentation often varies widely from the standardized descriptions of the applicable codes. For example, the coder might review a hospital report saying, "The patient coded at 5:23 pm." The coder must then apply the knowledge that "The patient coded" is hospital slang for a diagnosis of "cardiac arrest," which corresponds to ICD-9-CM code 427.5. This diagnosis could not have been identified from a simple word search for the term "cardiac arrest," since that standard term was not actually used in the documentation; more complex interpretation is required in this example. When coding in ICD-10, more specificity is required, and the coder may have to read and interpret other parts of the documentation to determine whether the cardiac arrest was due to an underlying cardiac condition (ICD-10-CM code I46.2), or due to a different underlying condition (ICD-10-CM code I46.8), or whether the cause of the cardiac arrest was not mentioned in the documentation (ICD-10-CM code I46.9), which might affect the level of reimbursement for any related services.

As also discussed above, conventional medical coding systems may provide a platform on which the human coder can read the relevant documents for a patient encounter, and an interface via which the human coder can manually input the appropriate codes to assign to the patient encounter. By contrast, some embodiments described herein may make use of a type of medical coding system referred to herein as a "computer-assisted coding" (CAC) system, which may automatically analyze medical documentation for a patient encounter to interpret the document text and derive standardized codes hypothesized to be applicable to the patient encounter. The automatically derived codes may then be suggested to the human coder, clinician, or other user of the CAC system. In some embodiments, the CAC system may make use of an NLU engine to analyze the documentation and derive suggested codes, such as through use of one or more components of a CLU system such as exemplary system 100 described above. In some embodiments, the NLU engine may be configured to derive standardized codes as a type of medical fact extracted from one or more documents for the patient encounter, and/or the CLU system may be configured to access coding rules corresponding to the standardized code set(s) and apply the coding rules to automatically extracted medical facts to derive the corresponding codes.

In some embodiments, the CAC system may be configured to provide a user interface via which the automatically suggested codes may be reviewed by a user such as a medical coder. For example, in some embodiments, a CAC system may be utilized in an operating environment similar to that shown in FIG. 1, in which the NLU engine may operate as part of fact extraction component 104, and a review/coding component may operate in place of or concurrently with fact review component 106. The user interface provided by the CAC system may take on any of numerous forms, and some embodiments are not limited to any particular implementation Like the user interfaces for the CLU system 100 described above, the user interface for the CAC system may provide tools that allow a coder to interact with the CAC system in any suitable form, including visual forms, audio forms, combined forms, or any other form providing the functionality described herein. When the tools are provided in visual form, their functionality may be accessed in some embodiments through a graphical user interface (GUI), which may be implemented in any suitable way in some embodiments and presented via one or more display devices. An example of a suitable GUI 700 for a CAC system is illustrated in FIG. 7A.

The exemplary GUI 700 provides the user with the ability to simultaneously view the list of codes for a patient encounter along with the documentation from which the NLU engine-suggested codes are derived. Some embodiments may also allow the user to view structured encounter- or patient-level data such as the patient's age, gender, etc. (not shown in FIG. 7A), some or all of which information may be useful in arriving at the appropriate codes for the patient encounter. In panel 710 is displayed a list of available documents for the patient encounter currently being coded. In the example illustrated in FIG. 7A, these include two History & Physical reports, a Discharge Summary, an Emergency Room Record, a Consultation report, a Progress Note, and an Operative Report. Indicator 712 shows that the current document being viewed is the Discharge Summary dated Jun. 18, 2014, and this document appears in panel 720 where the user can view the text of the document. Shown in panel 730 is the current list of codes being considered for the patient encounter. An indicator 732 shows, for each code in the list, whether the code was automatically suggested by the NLU engine, added manually by the user, or potentially received from another source. In this particular example, the empty circles indicate that all of the codes in the current list are engine-suggested codes that were automatically suggested by the CAC system.

Exemplary GUI 700 also provides the user with the ability to view and/or query which portion(s) of the available documentation gave rise to the suggestion of which code(s) in the list of codes for the patient encounter. In some embodiments, any suitable indicator(s) may be provided of the link between a particular code and the portion(s) of the documentation text from which the code was derived. Each automatically suggested code may be linked to one or more portions of text from which the code was derived, and each linked portion of text may be linked to one or more codes that are derivable from that portion of text. For instance, viewing together FIGS. 7A and 7D, which show the Discharge Summary viewed at different scroll locations in panel 720, it can be seen that there are two different mentions of "respiratory failure" in the document from which code 518.81 may have been derived (an example of a link between a code and multiple portions of text), and that there are two different codes 303.90 and 571.5 that may have been derived at least in part from the mention of "Alcoholism" in the text (an example of a link between a portion of text and multiple codes).

Figure 7C:
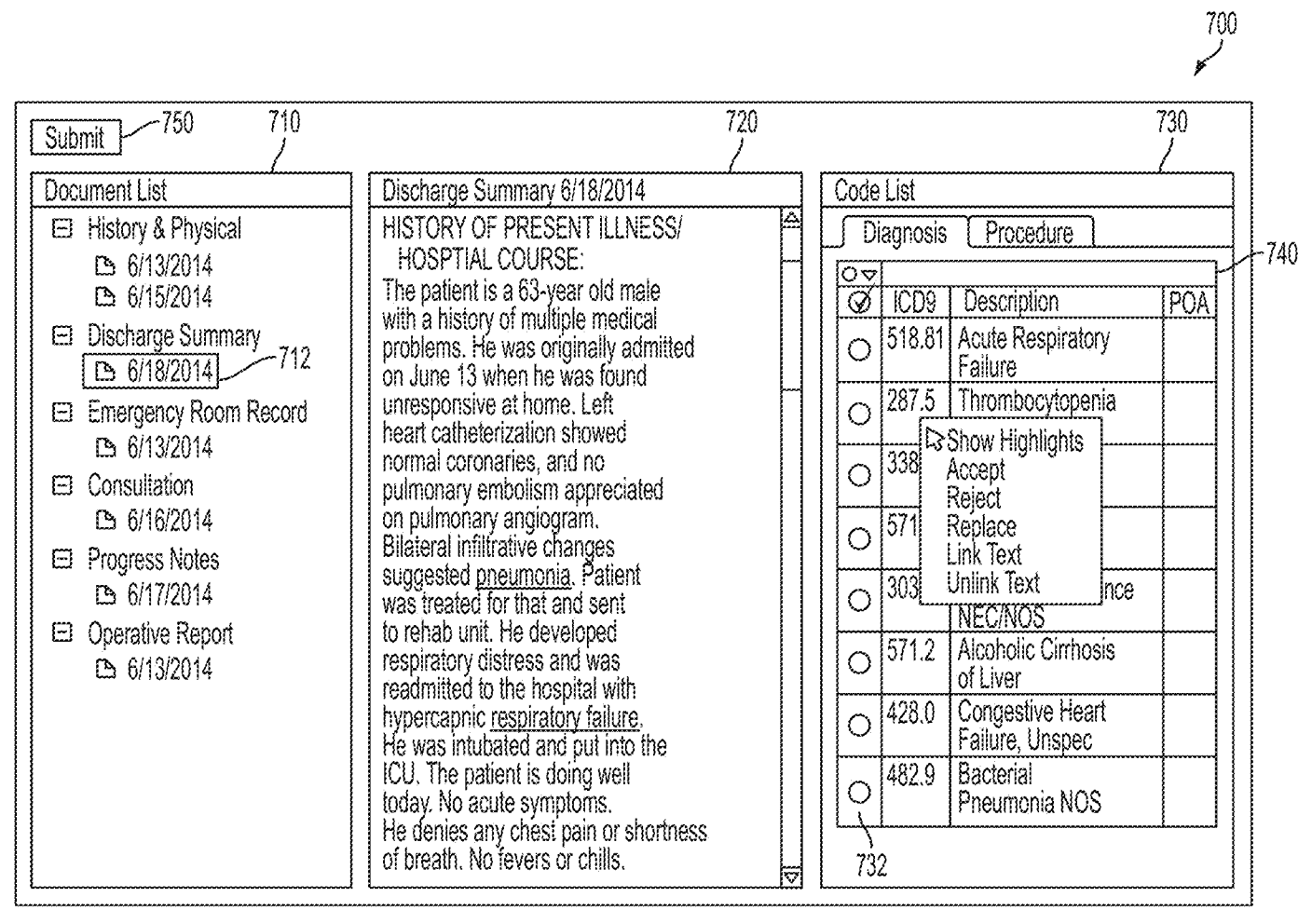

In the example of FIG. 7A, an indicator 722 is provided (underlining in this particular example) to visually distinguish portions of the document text linked to codes in the current list. Exemplary GUI 700 also allows the user to query a particular linked portion of text to see which code(s) are linked to that portion of text. FIG. 7B illustrates an exemplary indicator 724 of the corresponding link that may be displayed in response to the user querying the linked portion of text in any suitable way, such as by selecting or hovering over it with the mouse pointer. Exemplary GUI 700 further allows the user to query a particular code to see which portion(s) of text are linked to that code. FIG. 7C illustrates an exemplary way of querying code 287.5 by right-clicking on the listed code in panel 730 and selecting "Show Highlights" in the context menu that then appears. In response, the document in which the linked text appears is displayed in panel 720 (in this case it is the same Discharge Summary, scrolled to a particular section), and the linked text is visually distinguished by indicator 726 (highlighting in this particular example), as illustrated in FIG. 7D.

If the user disagrees with the linked text and does not believe that the suggested portion(s) of text actually should correspond with the linked code, the user can select "Unlink Text" in the context menu of FIG. 7C to cause the link between that code and the corresponding text to be discarded. The user can also manually create a new link between a code and one or more portions of text, e.g., by selecting "Link Text" in the context menu of FIG. 7C and highlighting or otherwise designating the portion(s) of text in the documentation which should be linked to the selected code. In some embodiments, when the user performs an action of this type, the action may be fed back as training to the NLU engine to improve its future associations of particular narrative text portions to particular billing codes.

Figure 7F:
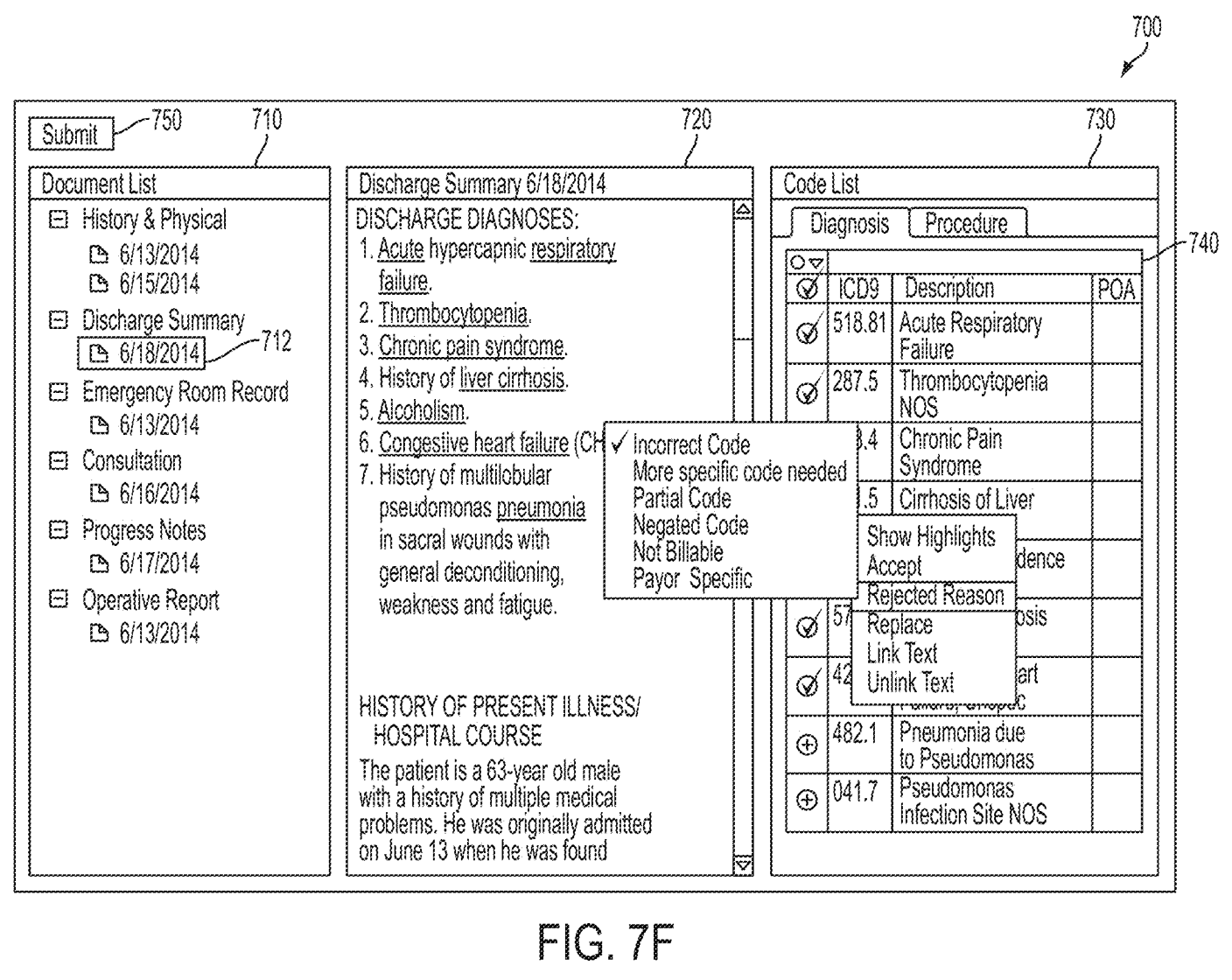

Exemplary GUI 700 further allows the user to accept or reject each of the automatically suggested codes, e.g., using the context menu of FIG. 7C for each suggested code. FIG. 7E illustrates exemplary indicators 734 and 736 which replace indicator 732 for each code that has been accepted or rejected, respectively. In this example, the user has accepted most of the suggested codes (making those accepted codes into user-approved codes), but has rejected code 571.5 because the user believes the mention of "Alcoholism" in the documentation makes the diagnosis of "Cirrhosis of Liver w/o Alcohol" incorrect. Exemplary GUI 700 further allows the user to provide a reason for the rejection of a code, such as by using the exemplary context menu illustrated in FIG. 7F. In some embodiments, the reasons provided by users for rejecting particular automatically suggested codes may be used for review and/or training purposes (e.g., for training the NLU engine, e.g., of the CLU system to derive more accurate codes from documentation text).

GUI 700 may also allow the user to replace a code with a different code, instead of rejecting the code outright, e.g., using the context menu of FIG. 7C. In the example illustrated in FIG. 7E, the user has replaced code 482.9 with code 482.1, and indicator 738 shows that the new code was user-added. 482.9 (Pneumonia due to *Pseudomonas*) is a more specific diagnosis applicable to the patient encounter than the suggested 482.1 (Bacterial Pneumonia, Unspecified), so the user may provide "More specific code needed" as the reason for the replacement. In some embodiments, when a user replaces an automatically suggested code with a different code, any documentation text that was linked to the originally suggested code may then be linked to the replacement code. Such replacement codes, optionally with linked text and/or replacement reasons, may also be used as feedback, e.g., for training of the CLU system. In some embodiments, identifier data may be associated with the replacement code to indicate that the code is a user-added replacement for an engine-suggested code, and data indicating the original engine-suggested code may also be tracked, to distinguish this code from other codes that may be user-added not as replacements for any engine-suggested codes. This identifier data may be maintained in association with the replacement code, to be used in determining how the replacement code, the engine-suggested code it replaced, and the linked document text will be used as feedback and further training for the NLU engine. Alternatively or additionally, in some embodiments the identifier data may be used to provide a symbol or other status indicator in association with the replacement code in the GUI 700 (not shown in FIG. 7E), letting the user know that this code 482.1 is a replacement code for an engine-suggested code, as opposed to a purely user-added code.

In some embodiments, when the user performs actions (i.e., enters user input) via the GUI to modify the currently presented set of engine-suggested medical billing codes for the patient encounter (e.g., in any of the ways described above), the user's modification of the engine-suggested codes may be used as feedback for adjusting the NLU engine. For example, the user modification of the presented set of engine-suggested codes may include rejecting an engine-suggested code and/or replacing an engine-suggested code with a different code. In this case, the action may be used as feedback to adjust the NLU engine to not suggest that code or similar codes in similar circumstances (e.g., from similar documentation text) going forward. In another example, the user modification may include rejecting and/or replacing a portion of the documentation text that the NLU engine linked to an engine-suggested code for the patient encounter. This user action may indicate that the linked text portion actually does not provide good evidence for the engine-suggested code being applicable to the patient encounter, and this may be used as feedback to adjust the NLU engine not to link similar text to that code or similar codes going forward. In another example, the user modification may include accepting (i.e., approving) an engine-suggested code, which may modify the engine-suggested code by changing its status from merely engine-suggested to user-approved. In this case, the action may be used as feedback to adjust the NLU engine to increase its propensity to suggest that code or similar codes in similar circumstances going forward, or to increase its confidence level in doing so, etc.

In some embodiments, feedback to the NLU engine based on user coding/review actions performed via the CAC GUI may occur during the coding of the patient encounter, as opposed to only after the coding is complete. For example, in some embodiments, the user modification to the current set of codes for the patient encounter that is used as feedback to adjust the NLU engine may result in a modified, unfinalized set of user-approved billing codes for the patient encounter. The set of codes at this point may be unfinalized because the user still has further codes to review, has further documents to review for the patient encounter, has not yet decided on the final sequence of the codes or the principal diagnosis, or simply is not ready yet to finalize the coding of the patient encounter for any suitable reason, etc. In some embodiments, feedback based on the user's actions in the CAC workspace may be used to adjust the NLU engine immediately after the actions are performed, even though the code set for the encounter is still unfinalized. In another example, the feedback may be provided to adjust the NLU engine when the user saves the current code set (in its unfinalized state), e.g., in order to take a break and return to the task of coding the patient encounter later.

In each of these examples, since the feedback based on the user's actions via the GUI may be used to adjust the NLU engine while the set of user-approved medical billing codes for the patient encounter is still unfinalized, in some embodiments the adjusted NLU engine may then be applied to automatically derive a new set of engine-suggested billing codes from the documentation of the encounter, and the new set of engine-suggested codes may be different from the previous set. For example, if the user rejected a particular code from the first set of engine-suggested codes, the NLU engine may be adjusted to learn from this and then suppress the suggestion of another same or similar code from a different part of the documentation in the same patient encounter. In another example, if the user replaced a particular code from the first set of engine-suggested codes with a different code (for example, a more specific code), the NLU engine may be adjusted accordingly and the adjusted engine may also change another same or similar code from a different part of the documentation of the same patient encounter to be similarly more specific. In some embodiments, when the new set of codes has been suggested by the adjusted NLU engine for the patient encounter from which the user modification feedback was received, the new set of codes may be presented for user review and consideration in the GUI before the coding of the patient encounter is finalized.

Any suitable technique(s) may be utilized to adjust the NLU engine based on the feedback from the coding/review process. Exemplary techniques for NLU engine adjustment based on user corrections in a CLU system are described in U.S. Pat. No. 8,694,335. The disclosure of that patent is hereby incorporated by reference herein in its entirety.

Exemplary GUI 700 also allows a user to add a code to the list for a patient encounter, independent of any of the engine-suggested codes, by manually inputting the user-added code in input field 740 of exemplary GUI 700. For example, FIG. 7E shows a new code 041.7 that has been added by the user. Exemplary GUI 700 also allows the user to link the added code to supporting portion(s) of the text, such as the mention of "*pseudomonas*" in the Discharge Summary, e.g., by using the "Link Text" procedure described above. This user input via the GUI thus communicates the user's identification of the linked portion of the text as providing evidence for the user-added code as being applicable to the patient encounter. A user may also manually link documentation text as supporting evidence for a replacement code. Alternatively or additionally, in some embodiments in response to receiving a user-added code, the CAC system may apply the NLU engine to automatically identify one or more portions of the documentation text as providing evidence for that code being applicable to the patient encounter. In some embodiments, when a user-added code is received, the CAC system may then automatically derive one or more additional engine-suggested codes that the user-added code makes applicable to the patient encounter, and may present those additional codes for user review. For example, the CAC system may have access to a set of coding rules for the standard code system that is being used (e.g., ICD, CPT, etc.), and those may include rules that trigger additional codes when base certain codes are entered (e.g., "code first" rules, "code also" rules, "use additional code" rules, etc.). In another example, a user-added code may cause the CAC system to suppress suggesting one or more other engine-suggested codes that are made inapplicable by the user-added code (e.g., because of an "excludes" rule associated with the user-added code).

Each of the foregoing is an example of a type of back-and-forth interaction between manual coding and automated NLU code suggestion and documentation that the inventors have appreciated may be made possible in an integrated application for both manual coding and user review of engine-suggested codes for a patient encounter. As illustrated in the example of FIG. 7E, in some embodiments the unified workspace of such an integrated CAC application may present both engine-suggested billing codes and user-added billing codes for a patient encounter in the same window in the GUI. In some embodiments, further, the source/status of each billing code in the workspace may be tracked (e.g., as user-added, engine-suggested, engine-suggested and user-approved, engine-suggested and user-rejected, received from an external source, etc.), and appropriate status indicators may be provided in the GUI (e.g., indicators 734, 736, 738). In some embodiments, some billing codes may be derived cooperatively by the NLU engine and the human coder. For example, in a case where the NLU engine is unable to arrive at a fully specified billing code (e.g., a final seven-character ICD-10 code), in some embodiments the NLU engine may suggest the first few digits of the code that it is able to determine automatically from the documentation text, and the coder may then complete the code manually via the GUI. In some embodiments, manual completion of an engine-suggested partial code may cause the status of the code to be changed from "engine-suggested" to "user-added," while the links to documentation evidence for the code as suggested by the NLU engine may be retained. In some embodiments, when the coder manually completes a code that the NLU engine suggested a partial version of, the coder may also have the opportunity to manually link one or more portions of the documentation text to the completed code as evidence, and/or the NLU engine may be applied to automatically identify one or more portions of the documentation text providing evidence for the manually completed code.

Similar to user actions on engine-suggested codes via the CAC GUI, in some embodiments, alternatively or additionally, user actions directed to user-added codes may be provided as learning feedback to the NLU engine during the coding of the patient encounter. For example, an initial set of engine-suggested codes for the patient encounter may be modified by the user by entering a user-added code into the current code set for the encounter. A further modification may be identification by the user of a portion of the documentation text as providing evidence for the user-added code as being applicable to the patient encounter. In some embodiments, such user actions may be used as feedback to adjust the NLU engine using any of the techniques discussed above, e.g., to make the NLU engine more likely to suggest the same or similar codes and/or evidence going forward, including in subsequently suggesting new codes for the same patient encounter and coding process. In some embodiments, adjusting the NLU engine may include training the NLU engine to automatically identify evidence in documentation text (i.e., one or more particular text portions) for the user-added code as being applicable to the patient encounter.

In some embodiments, there may be situations in which the user has already approved one or more codes for a patient encounter (e.g., by accepting one or more automatically-suggested codes with or without modification, or by manually inputting one or more codes) when the NLU engine (e.g., as part of the CLU system) derives one or more new codes for the same encounter. For instance, in one example, a new document may become available in document list 710 for a patient encounter after the coder has already been working on coding the encounter, and the NLU engine may be used to analyze the new document and derive one or more codes from it. In some embodiments, the new engine-derived codes may be compared with the previously user-approved codes to determine whether any of the new engine-derived codes should be filtered from presentation in code list 730. In some embodiments, an engine-derived code may be filtered from presentation when it is identified as overlapping with a user-approved code, in which case the engine-derived code need not be presented separately from the user-approved code in code list 730.

Medical billing codes may be identified as overlapping in any suitable way. In one example, an engine-derived diagnosis code may be identified as overlapping if it is the same code as a user-approved diagnosis code. In another example, an engine-derived procedure code may be identified as overlapping if it is the same code as a user-approved procedure code. However, in some embodiments, when a new engine-derived procedure code is the same code as a previously user-approved procedure code, a determination may be made, before filtering the engine-derived procedure code, as to whether the patient actually underwent the same procedure twice, and the new engine-derived code is for a different occurrence of the procedure than the previously user-approved code. In some embodiments, such a determination may be made automatically from the facts extracted from the documentation using the NLU engine. If the patient did undergo the same procedure twice, then in some embodiments both the user-approved procedure code and the engine-derived procedure code may be presented in code list 730, with separate links to corresponding textual documentation. If it is determined that the patient did not undergo the same procedure twice, then in some embodiments the new engine-derived procedure code may not be presented in code list 730 separately from the user-approved procedure code, since they refer to the same procedure that was performed only once on the patient.

In another example, an engine-derived code may be identified as overlapping with a user-approved code when the engine-derived code is a less specific version of the user-approved code. An example may be if the NLU engine derives a code for a bone fracture when the user has already approved a code for the same bone fracture plus dislocation. In some embodiments, the more specific user-approved code may be retained instead of the less specific engine-derived code, and the engine-derived code may not be presented in code list 730. In some embodiments, when a new engine-derived code is more specific than a previously user-approved code, then both codes may be presented in code list 730 for the user's review. In some embodiments, an alert may be provided to the user, indicating that a more specific code is available for consideration to replace the user-approved code.

In some embodiments, when an engine-derived code is determined to overlap with a user-approved code, the text linked to the engine-derived code (e.g., from the new document from which the engine-derived code was derived) may be linked to the user-approved code, e.g., by generating a new link between the user-approved code and the portion of text in the new document from which the engine-derived code was derived. In some such embodiments, when the user then selects the user-approved code (e.g., via the "Show Highlights" option in the context menu of FIG. 7C) in code list 730, an indicator of the newly linked text (corresponding to the engine-derived code) may be provided in document panel 720, e.g., by highlighting the text. In some embodiments, an alert may be provided to the user, indicating that additional documentation evidence (in the form of additional linked text) is now available in support of the user-approved code. In some embodiments, this may provide the user with further information to consider before finalizing the code set, and/or may provide enhanced documentation for later quality review and/or training purposes. In some embodiments, an alert may similarly be provided to the user when the NLU engine identifies new linked text in support of a previously user-rejected code.

In some embodiments, suggestion of a new engine-derived code may likewise be suppressed if the new engine-derived code is determined to overlap with a code that the user has already rejected or replaced while working on coding the patient encounter. In some embodiments, when a new engine-derived code overlaps with a previously rejected or replaced code, the new engine-derived code and its supporting documentation text may not be presented to the user, and may simply be discarded or may be retained in a data set and marked for suppression from the user interface. In other embodiments, however, the user may be provided with an alert that a new engine-derived code overlapping with a previously rejected or replaced code is available. The alert may provide the user with an opportunity to review the new engine-derived code and/or its supporting evidence, e.g., in case the new evidence might change the user's mind about the code and convince the user to accept the code as a user-approved billing code for the patient encounter. Similarly, in some embodiments, an alert may be provided when a document from the patient encounter is deleted or updated in a way that removes text that had been linked to a user-approved code for the patient encounter, so that the user may reconsider whether the code should still be approved given that some of its supporting evidence in the documentation has been deleted or changed.

In some embodiments, the CAC application and exemplary GUI 700 may additionally receive, track, and present one or more billing codes for a patient encounter that have been added external to the CAC GUI (i.e., outside of the CAC system). For example, such billing codes may have been added to the patient encounter directly through the patient's EHR or from any other suitable source (e.g., charge master codes, revenue codes, etc.). In some embodiments, these codes may be treated by the CAC system as user-added or user-approved codes, or as otherwise approved codes for the patient encounter. In some embodiments, in response to receiving such an externally added code, the CAC system may automatically determine whether the externally added code is a duplicate of an engine-suggested code in the patient encounter, e.g., by determining whether the externally added code overlaps with any engine-suggested code in any of the ways described above. In some embodiments, when it is determined that an externally added code is a duplicate of an engine-suggested code that has linked documentation text as supporting evidence, that portion of the documentation text may then be linked as well to the matching externally added code, and the engine-suggested code may be merged with the externally added code as a single user-approved code. In some embodiments, when an externally added code is not a duplicate and is not merged with any engine-suggested code, the externally added code may be treated as a user-approved code in the CAC workspace, but may be flagged so that it is not fed back to the NLU engine for adaptation/learning, since the externally added code may have been applied from another source and may not have any derivable evidentiary relationship with the documentation available to the NLU engine for the patient encounter. However, in some embodiments, externally added codes may trigger suggestion of additional engine-suggestion codes and/or suppression of suggestion of some engine-suggested codes based on coding rules (e.g., "code first," "code also," "use additional code," "excludes" rules, etc.). In some embodiments, externally added codes may alternatively or additionally be used by the NLU engine to make other engine-suggested codes more or less likely applicable to the patient encounter (e.g., changing the probabilities by which other codes are automatically derived from the documentation text and suggested).

Additional user interface techniques for allowing a user to interact with suggesting billing codes are described in U.S. application Ser. No. 15/372,338, titled "User Interfaces for Medical Documentation System Utilizing Automated Natural Language Understanding," and filed on Dec. 7, 2016, which is herein incorporated by reference in its entirety.

As discussed above, the inventors have appreciated that manual ordering of the suggested codes from the CAC is time intensive and tedious from the user perspective. To address this issue, the inventors have developed techniques for automatically determining a sequence for the medical codes suggested by an NLU engine (e.g., as part of a CLU system as described above) and providing the determined sequence to the user or customer. In particular, the inventors have developed a sequencing engine that orders the medical codes suggested, for example, by the NLU engine so that the user or customer does not have to manually order the medical codes from scratch. Instead, the user can review the suggested sequence for accuracy and make any changes necessary. Changes to the sequence of codes made by the user may be utilized as feedback to improve the performance of the sequencing engine and to learn the preferences of particular users (e.g., customers, institutions, etc.), as discussed in further detail below.

As discussed above, a CAC system may make use of the output from a trained NLU engine to provide information to the customer, for example, via a CAC application that suggests billing codes for the documentation of a patient encounter analyzed by the NLU engine. The CAC application may present the suggested billing codes via an interface, along with other relevant information such as links to the underlying medical facts or evidence supporting the respective billing codes, and may provide user interface functionality (e.g., a GUI) that allows the customer (e.g., a coder employed by the customer) to interact with the presented information (e.g., to view suggested billing codes and the supporting evidence in the documentation and to accept, reject, add, delete or otherwise edit or interact with the information). When the coder is finished editing and is comfortable with the results, the coder may finalize the set of codes for the patient encounter, which can then be sent, for example, to a payment provider to determine the level of reimbursement for the encounter according to set of codes that were accepted for submission.

Figure 8A:
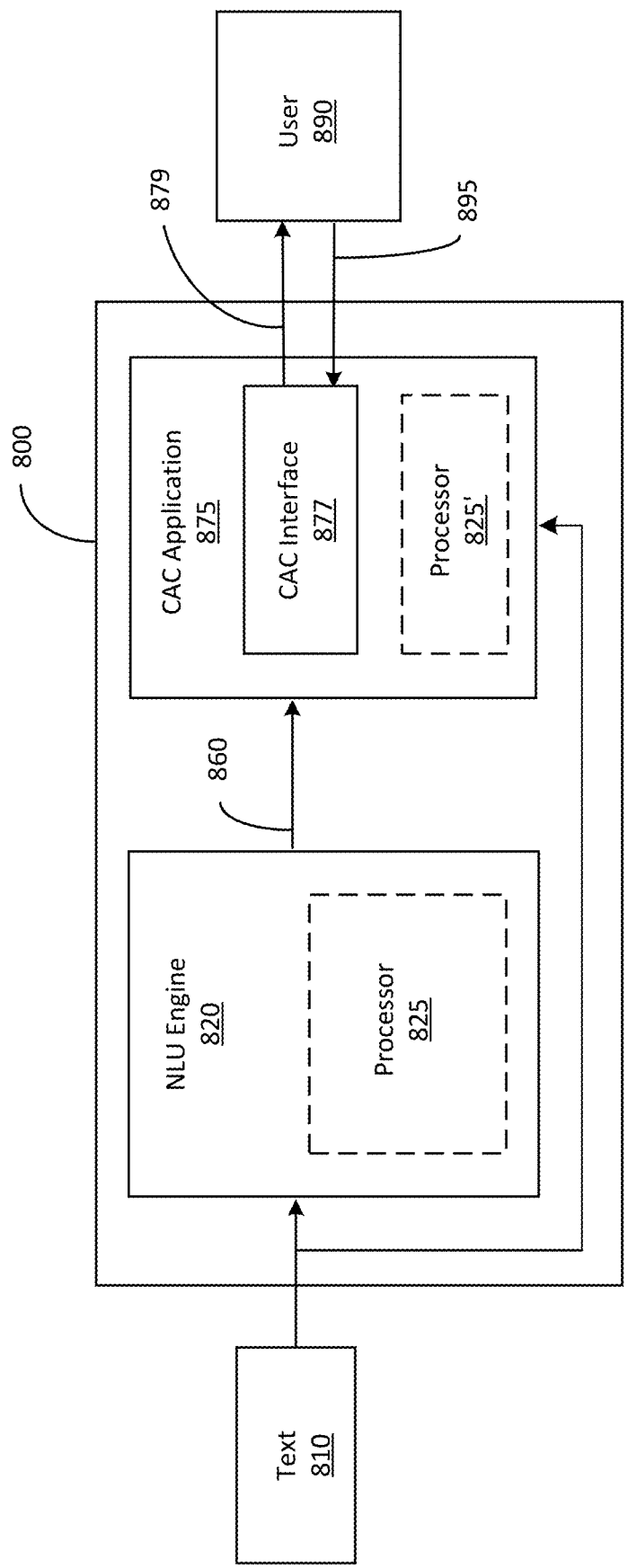
FIG. 8A is a block diagram of a CAC system for suggesting medical billing codes, in accordance with some embodiments.

FIG. 8A is a block diagram of a CAC system 800 that, among other functions, presents suggested billing codes to a user 890 for a text 810 (e.g., documentation of a patient encounter dictated or otherwise provided by a physician). CAC system 800 may make use of a NLU engine 820 (which may be implemented via a processor 825) to analyze text 810 to extract particular information provided to CAC application 875 (which may be implemented via processor '825) as annotations 860. As discussed above, the term "annotation" refers to information detected in and/or derived from a portion of text, such as facts (e.g., a medical fact, one particular example of which may be a medical code), semantic labels, relationships between facts and/or semantic labels, etc.). An annotation typically also includes a link or reference to the portion of text from which it was derived. Text 810 may include free-form text (in one or more documents) documenting one or more clinical patient encounters. The text 810 may be in any suitable format and may have been obtained from any suitable source. For example, text 810 may include a transcription of dictation from a physician documenting a patient encounter, transcribed using ASR, a human transcriptionist or a combination of both. Text 810 may include text input by medical personnel documenting a patient encounter, or may include other text for which extraction of facts, semantic meaning, etc., may be desired, as the aspects are not limited with respect to the source or the nature of text 810.

The NLU engine 820 may analyze the text 810 and generate annotations 860 that are provided to CAC application 875 as a basis for providing billing code suggestions 879 that are presented to user 890 via CAC interface 877. As an example, text 810 may include the sentence "These finding are likely related to diverticulitis." For this sentence, NLU engine 820 may produce the following annotations 860 for this portion of text 810. The term "diverticulitis" may be detected as a medical fact of type DISORDER, the word "likely" may be detected as a fact of type HEDGE, and the "likely" and "diverticulitis" may be identified as having a relationship to one another. NLU engine 820 may further assign an internal code to the medical fact "diverticulitis" extracted from text 810 (e.g., NLU engine 820 may assign the code 307496006, which is the SNOMED code for the disorder diverticulitis).

The above exemplary annotations extracted from this portion of text may then be provided (along with annotations extracted from other portions of the text being analyzed) in conjunction with text 810 (or portions of text 810 linked to by the annotations) to CAC application 875 to assess whether any billing code should be suggested to the user. For example, user 890 may be a customer that performs medical coding in accordance with ICD10 codes, and CAC application 875 may evaluate the above exemplary annotations to determine whether to suggest the ICD10 code of K57.92 corresponding to diverticulitis. That is, whether this portion of text documents a consequential billable event, or whether this mention of diverticulitis is inconsequential from a billing perspective. Similarly, CAC application 875 may assess all annotations 860 received from NLU engine in processing text 810 to determine the set of billing codes 879 to be presented to user 890 via CAC interface 877 for review and editing as needed.

As indicated above, NLU engine 820 may assign internal medical codes to facts extracted from text 810. These internal medical codes may differ from the billing codes suggested by the CAC application 875. For example, NLU engine 820 may assign SNOMED codes to medical facts and CAC application 875 may suggest one or more ICD10 codes to medical facts based on evaluating the annotations 860 (including the assigned SNOMED codes) produced by NLU engine 820. Use of internal medical codes may facilitate providing a customized CAC application 875 that can derive billing code suggestions in accordance with the particular set of coding standards utilized by the customer. However, it should be appreciated that internal medical codes need not differ from the billing codes suggested to the user, nor is the use of internal medical codes a requirement, as the techniques described herein are not limited for use with any particular representation utilized by the NLU engine and/or CAC application.

It should be appreciated that other relevant information, in addition to suggested billing codes 879, may be presented to the user via CAC interface 877. For example, CAC interface 877 may be similar to GUI 700 illustrated in FIGS. 7A-7G and may present any of the information and provide any of the functionality described in connection with GUI 700 to allow a user 890 to interact with the CAC system, for example, to accept one or more suggested billing codes, edit one or more billing codes, add or delete one or more billing codes, increase the specificity of a billing code (e.g., if the billing codes and links include a generic medical billing code for a fracture while the corresponding text also indicates a dislocation for the same clinical patient encounter, user 890 may replace the generic medical billing code for a fracture with a specific medical billing code for a fracture plus dislocation), or provide other feedback 895 to the CAC system via CAC interface 877 (e.g., reasons for a correction, modifications to the evidence supporting a billing code, etc.).

In addition to presenting the correct set of medical billing codes to the user, it is also important to correctly order the medical billing codes according to relevance or significance. Merely knowing the diagnoses may not be sufficient in certain circumstances and assessing the priority of the diagnoses and, more particularly, determining which is the principal diagnosis (e.g., the main reason for the patient visit to the hospital, clinic or doctor's office) and which represent complications or comorbidities may be required. Accordingly, identifying a primary billing code corresponding to the principal diagnoses is often a critical step in the patient care process. For example, identifying the principal diagnosis is often needed for reimbursement and therefore a critical first step in the medical billing process. Additionally, identification of the principal diagnosis is in important aspect of determining the patient's Diagnosis-Related Group (DRG), which in turn determines a health care provider's financial reimbursement for care, as discussed in further detail in connection with FIGS. 9A-9C. Moreover, accurately prioritizing billing codes may play an important role improving clinical documentation to support triage efforts, guide patient questioning and/or otherwise improve patient care.

Conventionally, the process of identifying the principal diagnosis and sequencing billing codes according to priority is performed with much effort by medical coding experts. The inventors have recognized the value of automatically sequencing medical billing codes and presenting the ordered sequence to a coder to reduce the burden of manually performing code sequencing. However, doing so presents significant technical challenges. Medical coders undergo significant training to be able to sequence billing codes, identify the principal diagnosis, determine a patient's DRG, etc. Training a sequencing engine to accurately perform these expert functions presents a technical problem that the inventors have solved by identifying a set of features that can be extracted from training data so that, for example, a machine learning model learns the context and characteristics needed to accurately sequence billing codes derived from documentation of a patient encounter. According to some embodiments, a primary billing code corresponding to the principal diagnosis is automatically identified and presented as the first billing code in a sequence of medical billing codes ordered by the sequencing engine (which may comprise one or more machine learning models), further detail of which is provided below.

Figure 8B:
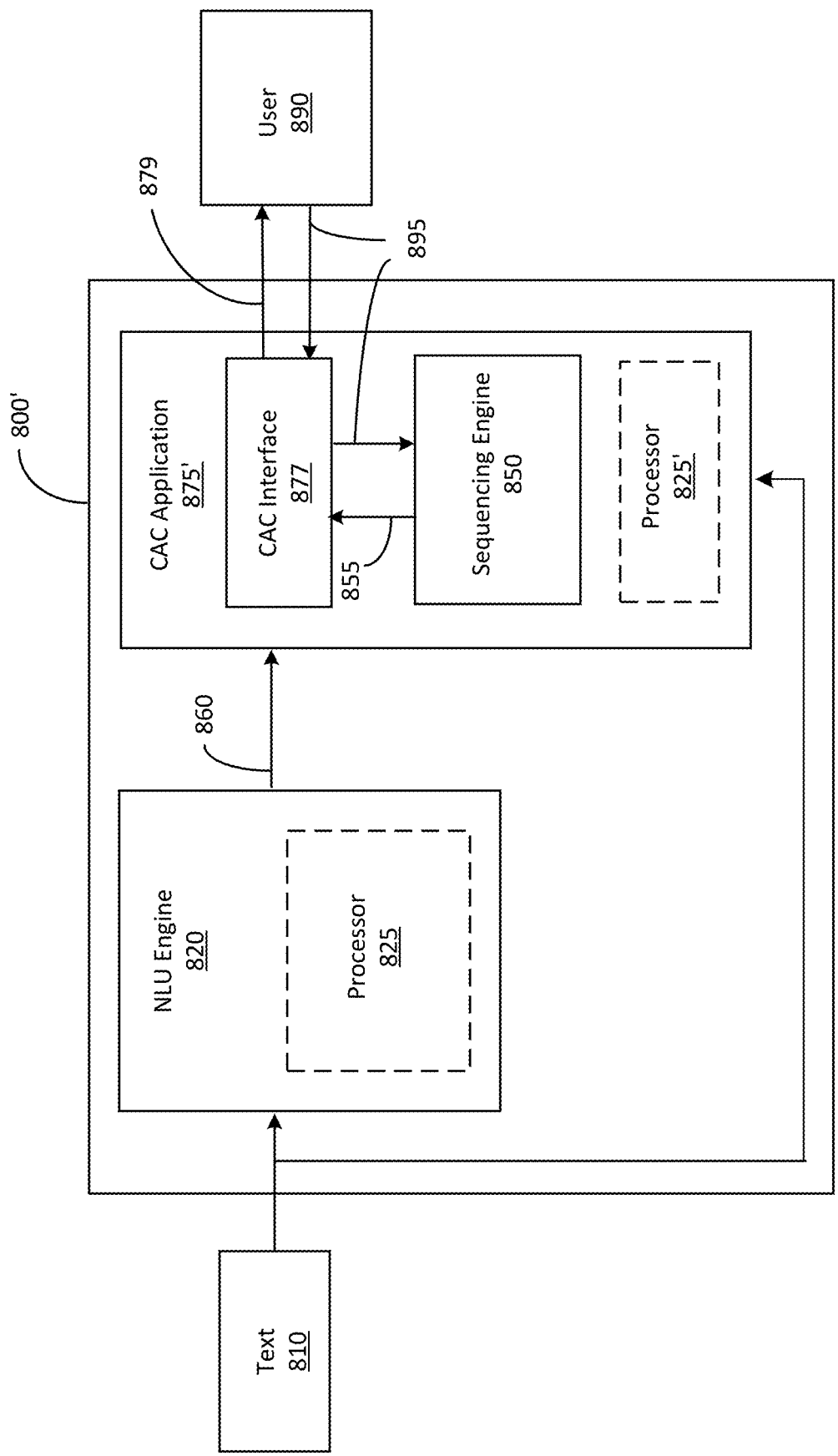
FIG. 8B is a block diagram of a CAC system including an exemplary sequencing engine, in accordance with some embodiments.

FIG. 8B illustrates a block diagram of a sequencing engine 850 trained to sequence medical codes suggested by NLU engine 820 for a patient encounter, in accordance with some embodiments. Sequencing engine 850 may be trained by providing training data from NLU engine 820 and/or from human annotators resulting from a corpus of free-form text of patient encounters, the training data including the annotations of the free-form text provided by the NLU engine 820 and, in particular, the medical codes derived from the free-form text along with other annotations such as any medical facts, semantic labels, links to corresponding portions of text from which it was or could be derived, etc. The output of the NLU engine 820 and/or human annotators is also manually sequenced by the human annotators to produce "ground truth" for the sequence of medical codes. The medical code sequences produced by the one or more human annotators are used by sequencing engine 850 to learn how to produce ordered sequences of medical codes from features produced by the NLU engine 820 and/or human annotators from patient encounter information, for example, free-form text automatically and/or manually transcribed from clinician dictation.

Training data may also include or be based on information associated with, or obtained as a result of, user 890 interacting with a CAC application 875'. As discussed above, user 890 may interact with CAC application 875' via a CAC interface 877 that allows user 890 to add, delete, modify, accept, reject and/or otherwise provide feedback 895 to CAC application 875' regarding the billing codes suggested by the CAC application. Specifically, in addition to editing the suggested billing codes, user 890 may also sequence the medical codes in order of priority, for example, beginning with the primary billing code representing the principal diagnosis and continuing down through secondary diagnoses (e.g., complications or comorbidities associated with the principal diagnosis). When the user is satisfied with the billing codes and their sequence, the user may submit a finalized billing code sequence (e.g., to obtain reimbursement). Thus, feedback 895, which may include the edits made by the user, the finalized ordered sequence of billing codes, etc., along with the corresponding patient documentation and/or associated annotations may be used as training data to train sequencing engine 850. In this manner, sequencing engine 850 can be trained in accordance with the coding preferences and practices of specific users (e.g., specific customers utilizing CAC system 800). According to some embodiments, a separate sequencing engine 850 is trained for each customer, though the aspects are not limited in this respect.

A trained sequencing engine 850 can then be used to sequence medical codes in a rank order according to learned priorities (e.g., in an order from a primary billing code corresponding to a principal diagnosis followed by one or more ordered second billing codes corresponding secondary diagnoses, such as complications or comorbidities associated with the principal diagnoses). Sequencing engine 850 can continue to be adapted to learn preferences of particular users via feedback from the users in correcting the sequences proposed by sequencing engine 850. That is, user feedback may be used to initially train the sequencing engine 850 and to adapt the sequencing engine via further training as additional feedback is obtained from user 890 in the course of utilizing CAC system 800', as discussed in further detail below.

CAC system 800' illustrated in FIG. 8B, once trained, may operate in production as follows. Text 810 corresponding to a patient encounter, which may be transcribed either automatically (e.g., via ASR) and/or manually (e.g., via a human transcriber) from clinician dictation or otherwise obtained (e.g., as text input from a clinician), is provided to NLU engine 820. For example, NLU engine 820 may be of the type described in the foregoing and may be part of a CLU system as described in connection with FIG. 1. NLU engine 820 may annotate text 810 in any manner described herein and at least some of the annotated text may be provided as features, which include the medical codes generated by NLU engine 820 based on analysis of text 810, to sequencing engine 850 for ordering. Based on the features, sequencing engine 850 provides an ordered sequence of medical codes 855 to CAC interface 877 (e.g., a CAC interface as described in connection with FIGS. 7A-7F). For example, sequencing engine 850 may generate medical codes to present to a user in panel 730 of GUI 700 illustrated in FIG. 7A described above, but with the medical codes ordered in the sequence determined by sequencing engine 850 to ease the burden on the user in manually sequencing the medical codes.

The inventors have further appreciated that user feedback may be used to improve the performance of sequencing engine 850 and/or NLU engine 820. For example, any changes to the medical codes determined by NLU engine 820 and/or the medical code sequence determined therefrom by sequencing engine 850 may be used to adapt the respective engines to improve performance. In particular, changes made to the sequence of medical codes as generated by sequencing engine 850 can be provided as feedback 895 to, along with the corresponding features, adapt sequencing engine 850. That is, feedback 895 along with the corresponding features associated with the billing codes in medical code sequence 855 can be used as additional training data to train sequencing engine 850. Because feedback 895 is user/customer specific, a sequencing engine may learn the preferences of a particular user (e.g., a customer, such as an institution, that has specific coding guidelines). In this manner, a given sequencing engine 850 can over time be customized to generate medical code sequences in a manner consistent with the preferences of the user/customer. Similarly, changes a user makes to the medical codes themselves (e.g., by removing and/or adding a medical code) may be provided as feedback 895 to NLU engine 820 to improve the performance of the engine in automatically generating medical codes from a given text, as discussed in further detail below in connection with FIGS. 10-15.

Conventional systems that automatically sequence medical codes rely on a rule-based approach, using hard-coded, fixed rules to order a set of medical codes into a suggested sequence. This approach has several drawbacks, among them the inability to adapt to new data and/or to tailor sequencing to particular user preferences or behavior. In addition, rule-based approaches are complex and difficult to implement. Accordingly, conventional techniques have numerous problems and drawbacks. The inventors have solved problems of rule-based approaches by developing techniques for producing a sequencing engine that utilizes a statistical model classifier to produce a medical code sequence. The statistical model classifier may be trained using a feature set obtained from an NLU engine, human annotators, user/customer feedback and/or other information relevant to a patient encounter from which the feature set was obtained. The inventors have identified features to include in the feature set that allows a statistical model (e.g., as part of a sequencing engine 850) to be trained to accurately order medical billing codes according to priority, including one or more features that facilitate identifying a primary billing code representing a principal diagnosis. The feature set includes the medical codes generated from a patient encounter as well as other features providing information regarding the appropriate ordering of the medical codes.

According to some embodiments, the feature set includes one or any combination of the medical codes in the patient encounter (e.g., the set of medical codes generated by the NLU engine and/or generated by one or more human coders), the textual evidence underlying the medical code (e.g., the section from which the medical code was derived, the position within a section of one or more facts from which the medical code was derived, the type of document, etc.), historical ordering for a particular user/customer, indicators from one or more external sources regarding the importance of the code, etc. During training, weights of the statistical model are iteratively adjusted so that medical code sequences that are consistent with, correspond to and/or match the medical code sequences produced by human coders or received from customers editing or reordering a medical code sequence is achieved. Because the training data can include sequences from actual user/customers, a statistical model can learn the preferences and behaviors of particular user/customers, as discussed in further detail below. During deployment, the trained sequencing engine (e.g., sequencing engine 850) produces medical code sequences from medical codes generated from respective patient encounters (e.g., by an NLU engine of a CLU system), and any edits, corrections, additions and/or subtractions from human users reviewing the sequence produced by the sequencing engine can be fed back and utilized as further training data to adapt a given sequencing engine to the particular user/customer. In this manner, a sequencing engine can learn the preferences and behavior of particular users/customers.

Figure 8C:
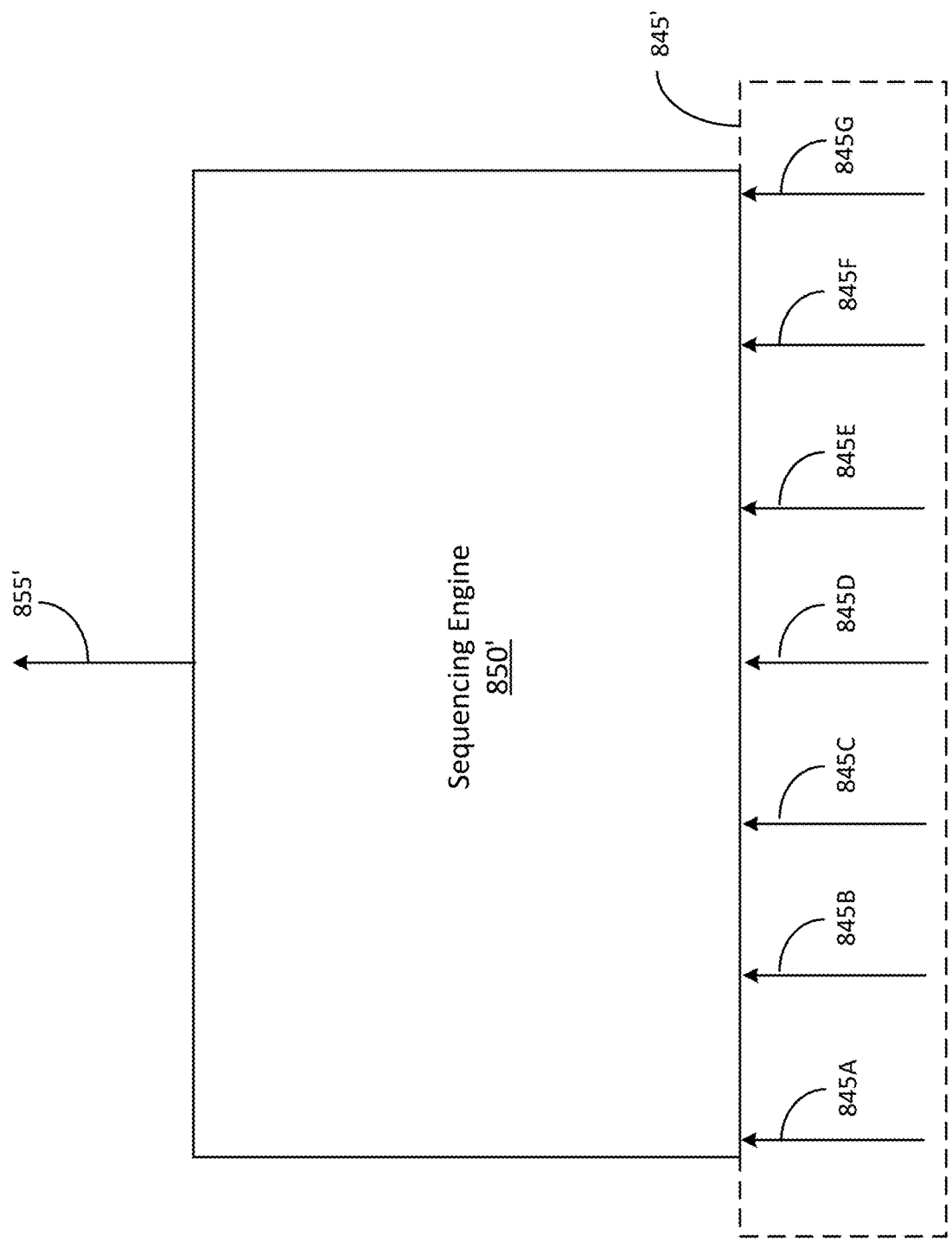
FIG. 8C is a block diagram a sequencing engine illustrating exemplary features that may be used to train the sequencing engine and/or to determine an ordered sequence of medical billing codes during use.
Figure 10:
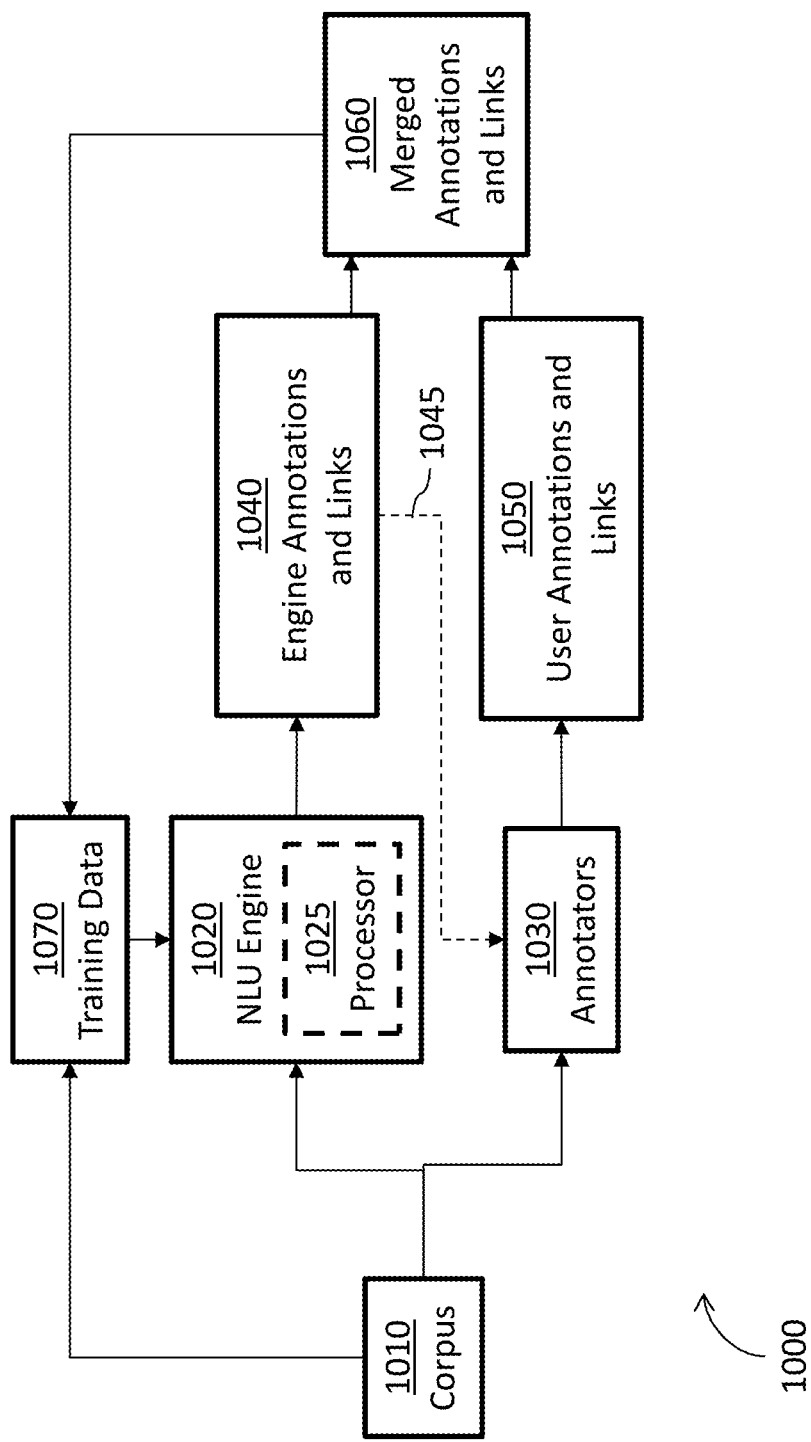
FIG. 10 is a block diagram of a system for training a natural language understanding (NLU) engine in accordance with some embodiments.
Figure 11:
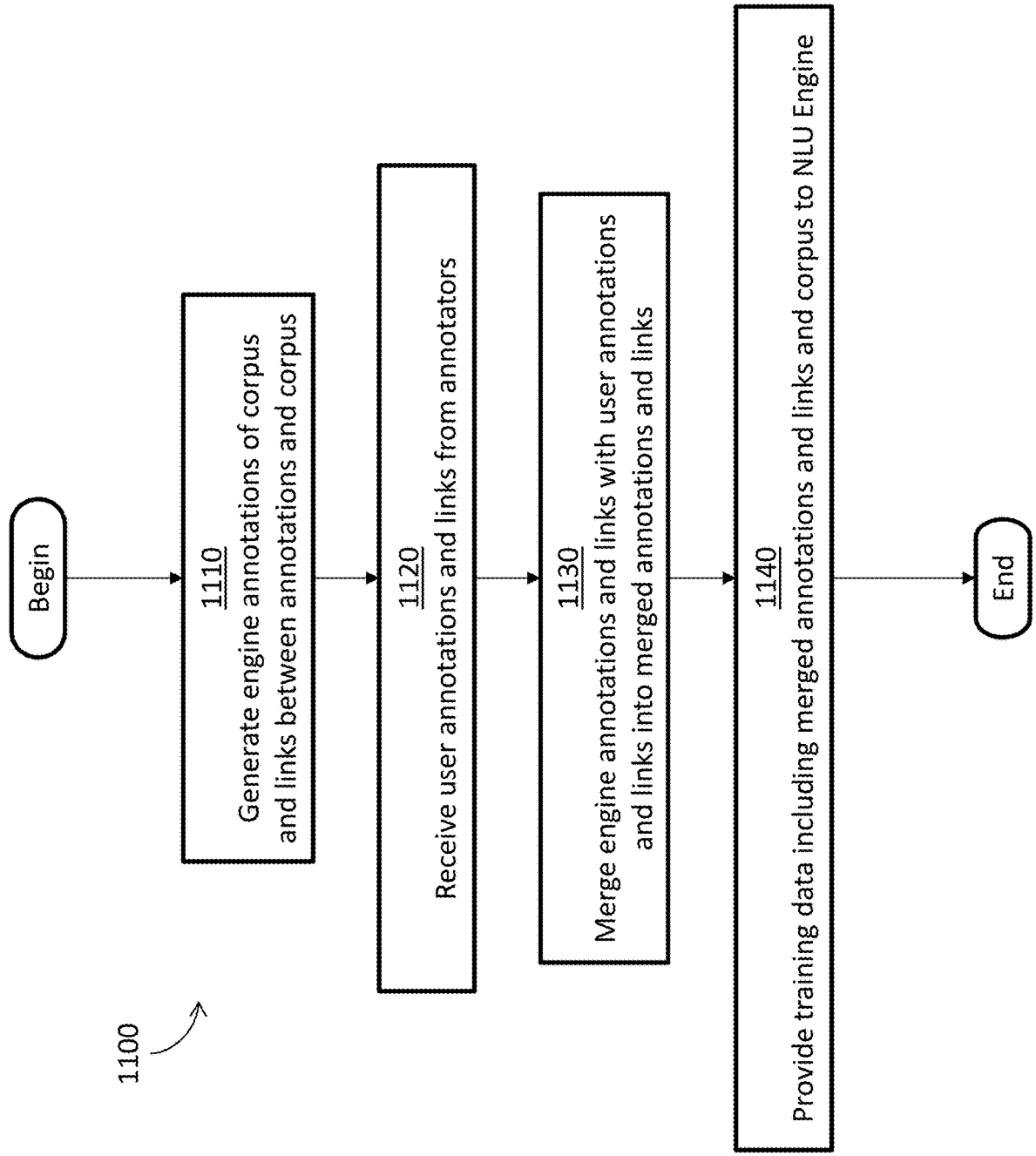
FIG. 11 is a flowchart of a method for training a NLU engine in accordance with some embodiments.
Figure 12:
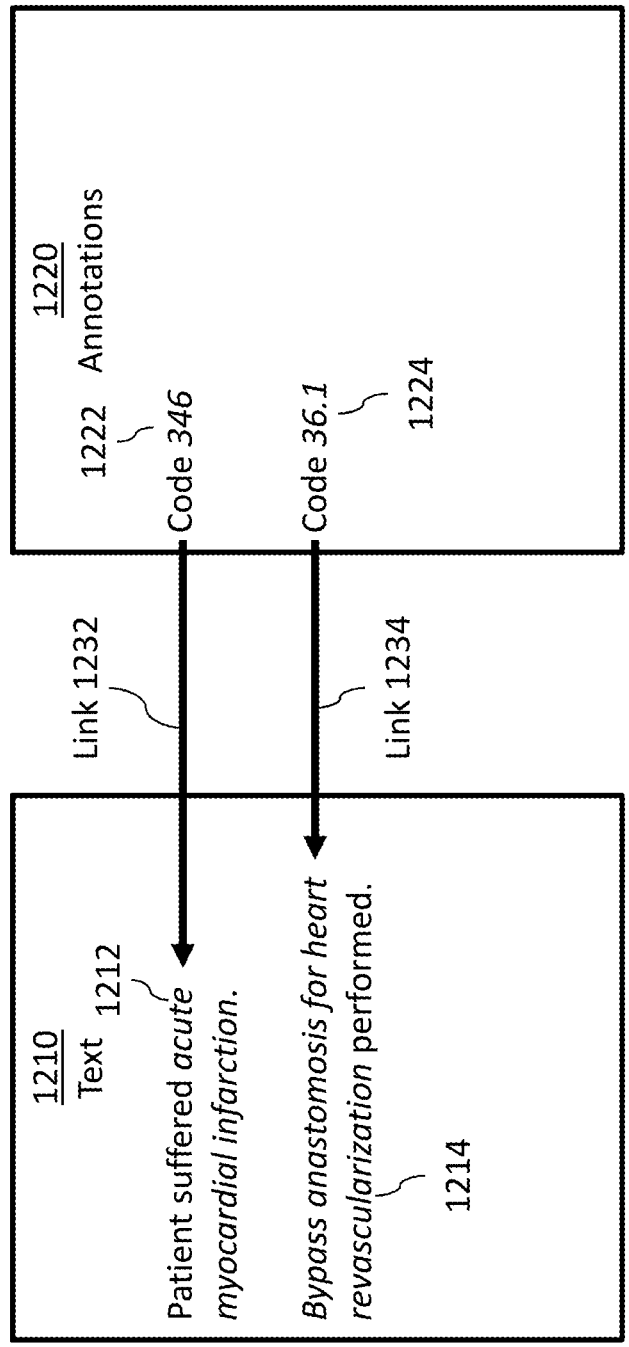
FIG. 12 illustrates an example of text and corresponding annotations and links in accordance with some embodiments.
Figure 13:
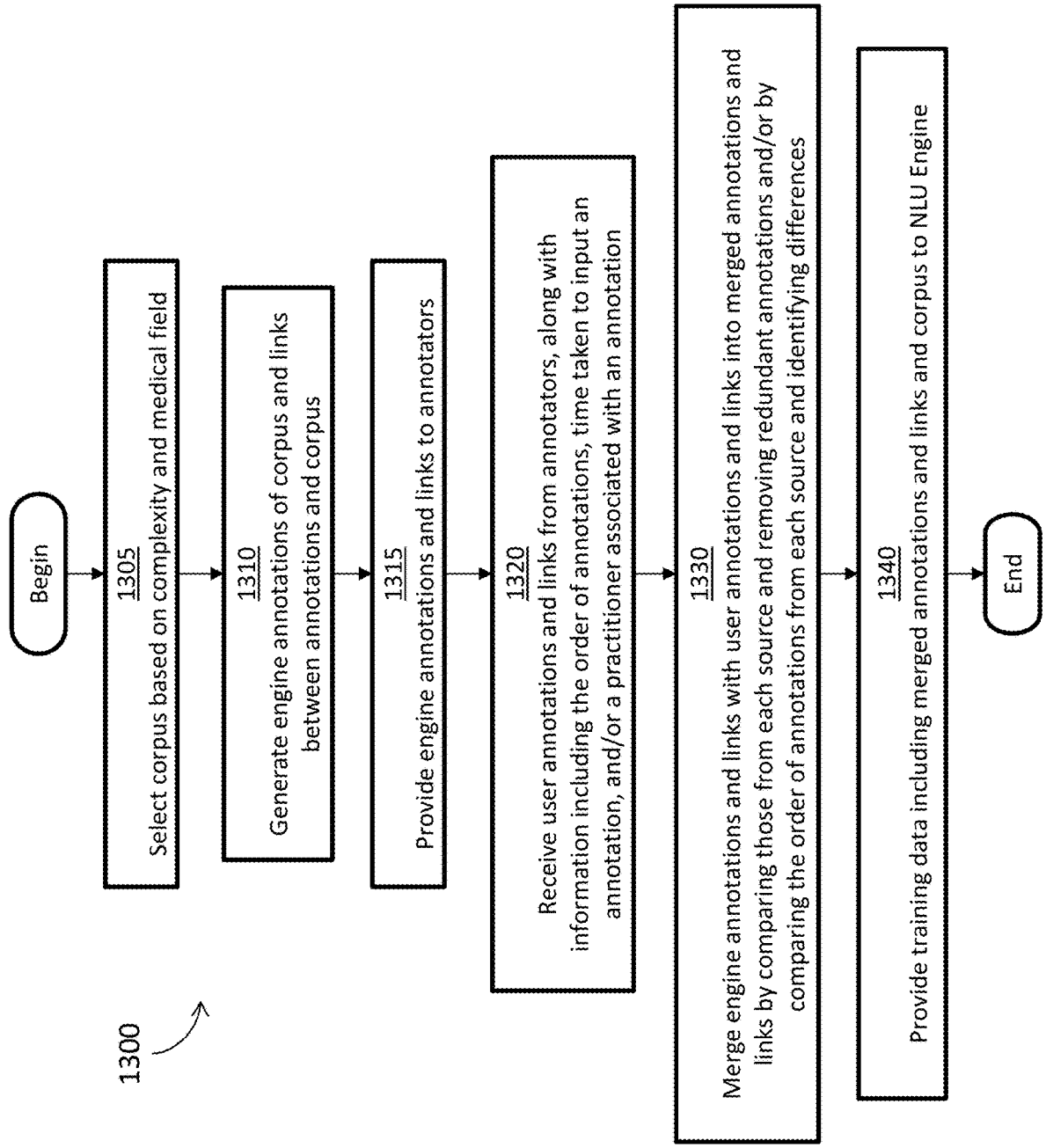
FIG. 13 is a flowchart of a method for training a NLU engine in accordance with some embodiments.
Figure 14:
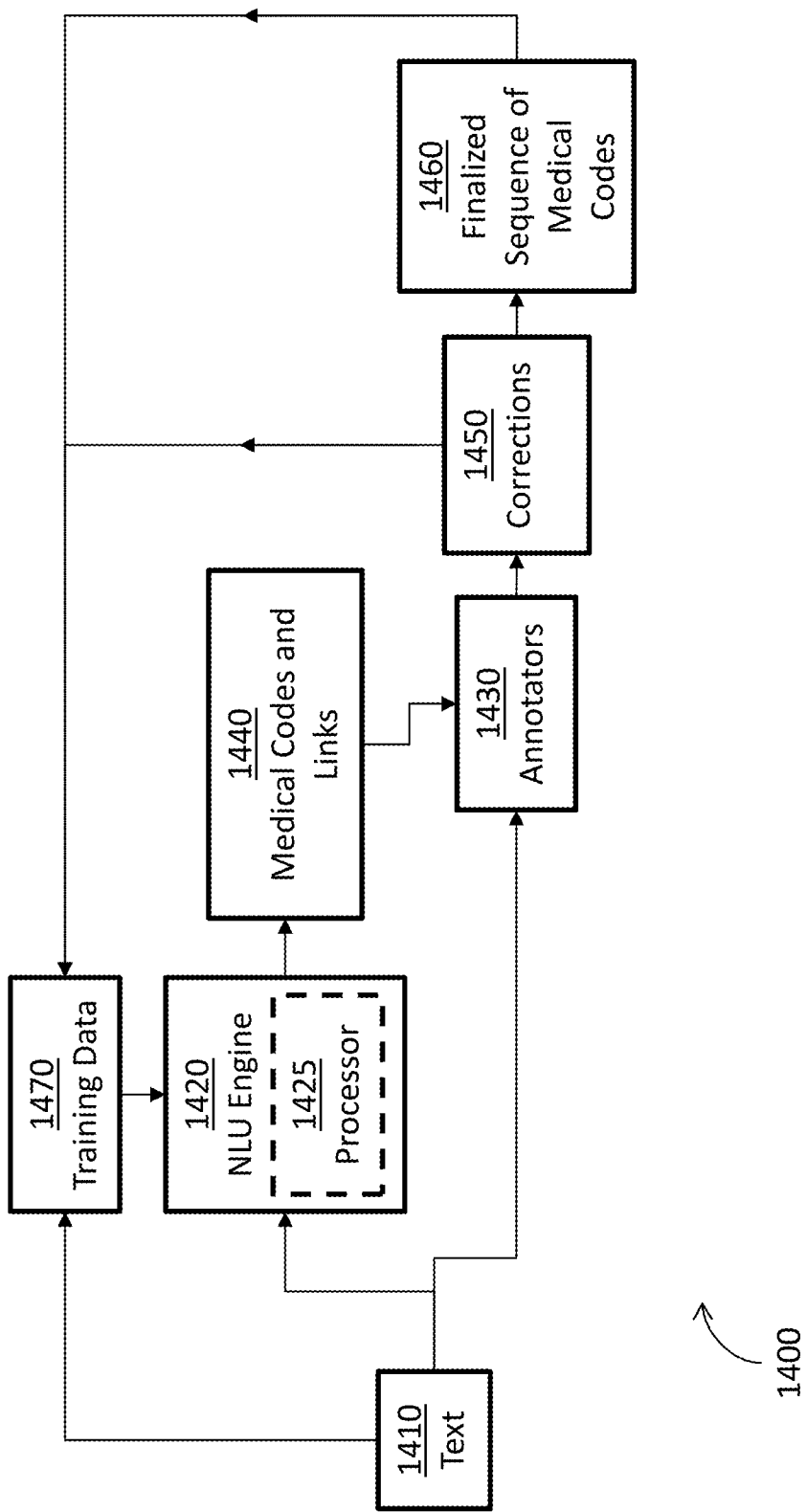
FIG. 14 is a block diagram of an alternative system to that of FIG. 10 for training a NLU engine in accordance with some embodiments.
Figure 15:
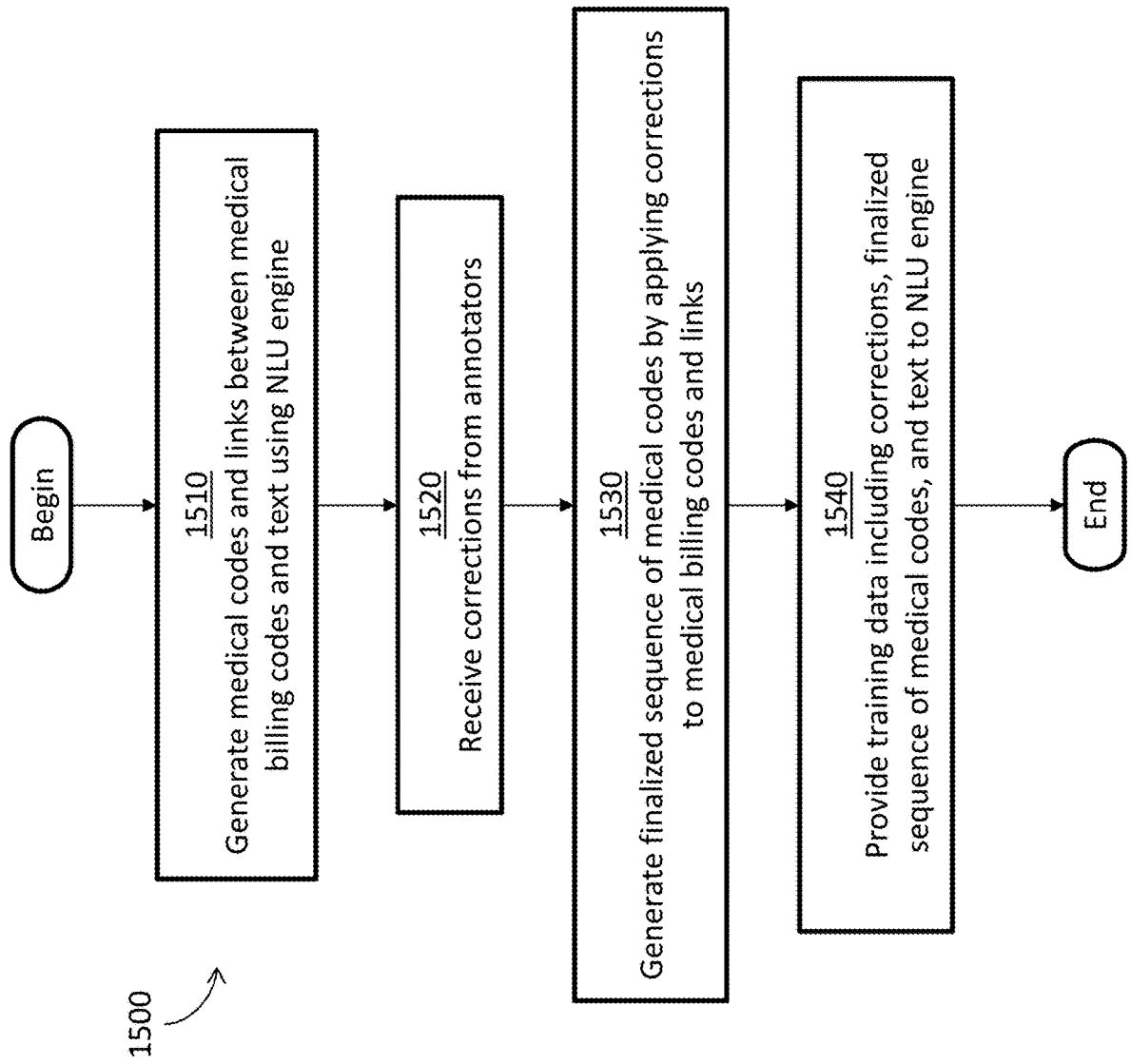
FIG. 15 is a flowchart of a method for training a NLU engine that may be implemented with the system of FIG. 14 in accordance with some embodiments.

Following below is a description of an exemplary feature set used by a sequencing engine, in accordance with some embodiments. FIG. 8C illustrates an exemplary feature set 845' that may be provided to sequencing engine 850', which may operate, once trained, in a manner similar to sequencing engine 850 described in connection with FIG. 8A. Feature set 845' may include exemplary features 845A-G, each of which is described in further detail below.

Exemplary features 845A represent the one or more medical codes generated for a given patient encounter (e.g., generated by an NLU engine of a CLU system as discussed in the foregoing). According to some embodiments, features 845A comprise a binary feature for each medical code for which meaningful training data has been obtained. For example, for each of a plurality of medical codes for which sequencing engine 850' has been exposed to sufficient training data, features 845A includes a binary feature indicating whether the corresponding medical code is present in the set of medical codes determined for the corresponding patient encounter (e.g., a feature 845A may be a "1" if the corresponding medical code is present and a "0" if the corresponding medical code is not present). For example, a feature 845A may comprise a vector of length n, where n is the number of medical codes on which the sequencing engine is being trained (e.g., between 1,000 and 2,000 individual medical codes) and wherein each vector component corresponds to one of the represented medical codes. Thus, for a given medical code extracted from documentation of a patient encounter in the training data, feature 845A may include a "0" for all vector components, except that the vector component corresponding to the given medical code will be assigned a "1". It should be appreciated that any number of medical codes can be represented by features provided to the sequencing engine, as the aspects are not limited in this respect. Additionally, the number of codes represented by features 845A may change over time, for example, as additional codes are represented in the training data.

Exemplary features 845B comprise co-occurrence pairs of medical codes co-occurring with another medical code (e.g., wherein both codes are possible principal or primary diagnoses). For example, features 845B may include a feature for each pair of medical codes represented by features 845A that are found in a Principal Diagnosis list discussed in further detail below. For example, an exemplary feature 845B may also comprise a vector of length n, where n is the number of medical codes on which the sequencing engine is being trained and wherein each vector component corresponds to one of the represented medical codes. Thus, for a given medical code extracted from documentation of a patient encounter in the training data, feature 845B may include a "1" for all vector components corresponding to medical codes for which the given medical code is listed as a co-occurrence pair, and all other vector components may be assigned a "0". Any number of co-occurrence pairs may be chosen and are not limited to pairs that appear in a Principal Diagnosis list, as the features 845B may represent other types of co-occurrence pairs that are deemed of interest in sequencing billing codes. According to some embodiments, features 845B include a binary feature for between 500 and 1,000 co-occurrence pairs of medical codes. According to some embodiments, features 845B include a binary feature for less than 500 occurrence pairs of medical codes and, according to some embodiments, features 845B include a binary feature for more than 1,000 co-occurrence pairs of medical codes.

Exemplary features 845C comprise information indicating from which section of documentation of a patient encounter a target medical code was derived. In particular, for a given medical code indicated in a feature 845A, a corresponding feature 845C indicates which section of the documentation of the patient encounter the respective medical code was derived. For example, features 845C may represent sections such as "Assessment and Plan," "Social History," "Past Medical History," "Reason for Admission," "History of Present Illness," etc. Similar to other features described above, features 845C may represent a binary feature indicating whether a given medical code was derived from the corresponding section. In this way, if a medical code was derived from more than one section, features 845C can capture and utilize this information in determining the importance (e.g., order) of the medical code in the sequence. Any number of sections may be represented as a feature 845C, as the aspects are not limited in this respect.

Exemplary features 845D comprise information indicating where in a given section of documentation of a patient encounter a given medical billing code was derived. The inventors have recognized that clinicians tend to discuss principal diagnoses first in a given section. Thus, where in a section the facts that gave rise to a given billing code may provide some indication as to whether the billing code represents the principal diagnosis or represents a secondary diagnosis (e.g., a complication or comorbidity associated with the principal diagnosis). According to some embodiments, the text of a given section is partitioned into a number of regions and an exemplary feature 845D comprises a vector having a component for each region into which the section text is partitioned. For a given medical billing code, the feature vector may be assigned a value of "1" for the component corresponding to the region from which the medical billing code was derived and a "0" for the remaining vector components. In this manner, a feature vector 845D indicates where in the section a billing code was derived. It should be appreciated that a section can be partitioned into any number of regions to provide a desired level of granularity. For example, the text of a given section may be partitioned into three regions corresponding to the beginning, middle and end of the section text. Additional regions may also be included in the feature representation such as representation of whether a billing code was derived from the first sentence or phrase, whether the given medical billing code was the first medical billing code derived from the section, etc., or any other suitable partitioning of the section. According to some embodiments, features 845D may include a feature vector for each section in the documentation of the patient encounter, while in some embodiments, features 845D include a feature vector for a subset of the sections, or even a single section (e.g., the "Assessment and Plan" section), as exemplary features 845D are not limited for use to any one or combination of sections in the patient encounter documentation or to any particular partitioning of the sections.

Features 845E comprise information regarding the document type from which the medical codes were derived. For example, features 845D may represent document types such as "Labor Delivery Note," "Operative Note," "Progress Note," "Consultation," "History and Physical," "Procedure Note," "Discharge Summary," "Emergency Room Report," "Mental Health Note," etc. As with other features described above, features 845D may represent a binary feature indicating the document type of a target code. Any number of document types may be represented as a feature 845E, as the aspects are not limited in this respect. For example, any document type that the NLU engine understands may be included as a document type feature.

Features 845F comprise knowledge-based features about target codes, for example, using external resources. Features 845E may include indications about the importance of the codes using one or more external lists. For example, features 845F may comprise features indicating whether and/or how a target medical code is listed in classifications compiled by the Centers for Medicare and Medicaid Services (CMS) including, but not limited to, features indicating whether the target code is in the Major Complications and Comorbidities (MCC) list, whether the target code is in the Complications and Comorbidities (CC) list, whether the target code is in the Principal Diagnosis (PDX) code list, whether the target code is in the Secondary Diagnosis (SDX) code list, etc. Any number and/or type of knowledge-based features may be represented as a feature 845F, as the aspects are not limited in this respect. The external resources may, for example, include one or more resources utilized by a user/customer, such as customer or institution-specific coding guidelines.

Features 845G comprise historical statistics of feedback from user/customers. For example, features 845G may comprise historical features obtained over a predetermined interval (e.g., 6 months) indicating the probability or frequency at which the target code appears in the top 10% rank for a patient encounter, the probability or frequency at which the target code appears in the top 33% (top ⅓) rank for a patient encounter, the probability or frequency of which the target code appears in the top 50% rank for a patient encounter, the probability or frequency of which the target code is ranked as the top 1 code in an encounter, for example, how often the target medical code is identified as the principal diagnosis. According to some embodiments, the historical statistics may be computed from a larger database of information than used to train the sequencing engine 850'. The historical statistics can be updated as frequently or infrequently as desired to capture the most recent and/or relevant statistics. It should be appreciated that any historical statistic or feature may be represented as a feature 845G, as the aspects are not limited in this respect.

It should be appreciated that the above features are those that the inventors appreciated, when used alone or in any combination, were efficacious in training a sequencing engine. However, more, fewer or different features may be used to train a sequencing engine and utilized during operation/deployment of the sequencing engine to sequence codes determined for a patient encounter (e.g., by an NLU engine of a CLU system as described above), as the aspects are not limited in this respect.

As discussed above, a sequencing engine may be trained by developing a statistical model from a corpus of training data including numerous patient encounters for which the selected set of features have been extracted. The sequencing engine may be exposed to the feature set extracted from each patient encounter in the training corpus to learn feature statistics and to sequence the medical codes accordingly. According to some embodiments, the sequencing engine includes a classifier that determines the likelihood that each medical code belongs to each of a plurality of classes or classifications. That is, the sequencing engine may produce an output 855' that indications that classifies the input and/or provides a confidence in the classification. For example, an exemplary classifier may include a first classification that the target medical code is ordered (e.g., ranked according to priority) in the top half of the medical codes determined for a given patient encounter and a second classification that the target medical code is ordered (e.g., ranked according to priority) in the bottom half of the medical codes determined for the given patient encounter. Such an exemplary classifier may evaluate the likelihood that each medical code determined for a patient encounter belongs to the first classification and the second classification. According to some embodiments, a maximum entropy statistical model is used to implement the classifier, though any suitable technique may be used, as the aspects are not limited to any particular machine learning technique.

As another example, an exemplary classifier may include a first classification that the target medical code is a primary billing code representing the principal diagnosis and a second classification that the target medical code is a secondary billing code representing a secondary diagnosis, complication, comorbidity, etc. Thus, such an exemplary classifier may evaluate the likelihood that each medical code determined for a patient encounter corresponds to the principal diagnosis. Such a classifier may be particularly beneficial in improving the performance of the sequencing engine in correctly identifying the primary billing code, which for some customers is the most valuable determination made by the sequencing engine. It should be appreciated that other classifications may be used, as the aspects are not limited in this respect.

The ordered sequence of medical codes may then be determined based on the likelihood values determined by the classifier of the sequencing engine. For example, according to some embodiments, the sequencing engine may rank-order the medical codes according to the likelihood that each medical code belongs to the first and second classification. In particular, according to such an embodiment, the medical code having the highest likelihood of belonging to the first classification may be ranked first in the sequence, the medical code having the second highest likelihood of belonging to the first classification may be ranked next and so on to the end of the sequence, where the medical code having the highest likelihood of being in the second classification (i.e., the medical code that is most likely to be in the bottom half of the medical codes) is ranked last in the sequence. Other techniques for using the likelihood values may be used to order the medical codes in a sequence, as the aspects are not limited in this respect. After training a sequencing engine (e.g., by extracting features associated with each medical billing code derived from a corpus of training data and inputting the features to sequencing engine 850' as discussed in connection with FIG. 8C), the trained sequencing engine (e.g., sequencing engine 850 illustrated in FIG. 8B) may be utilized to determine a rank order of medical billing codes from a target text (e.g., text 810). For example, referring again to FIG. 8B, annotations 860 (including medical codes derived from the text) from NLU engine 820, the corresponding text 810 and/or any external sources that are used, may be provided to CAC application 875' that, in turn, produces a set of billing codes to suggest to the user that can be ordered by sequencing engine 850. For example, a feature set may be extracted (e.g., exemplary features 845' illustrated in FIG. 8C) for each billing code suggested by CAC application '875 and each feature set may be input to sequencing engine 850 in turn. Sequencing engine 850 produces an output (e.g., classification 855' illustrated in FIG. 8C) corresponding to each respective feature set, the collection of which may be analyzed to produce an ordered sequence 855 of the billing codes. This ordered sequence of billing codes, beginning with or otherwise identifying a primary billing code representing the principal diagnosis, may be presented to the user for review.

FIG. 7G illustrates an example of an ordered sequence of medical codes produced by a sequencing engine according to any of the techniques described herein. In particular, medical codes determined for a patient encounter may displayed in screen 700' in an ordered sequence 755 determined by sequencing engine (e.g., sequencing engine 850 or 850'). Display screen 700' may be presented to a user/customer as part of a CAC interface (e.g., as panel 730 described in connection with FIGS. 7A-7F). As a result, sequencing engine may obviate at least some (and in some cases all, particularly as the sequencing engine learns user/customer preferences over time) of the adjusting of the medical code sequence conventionally performed by the user/customer.

In some embodiments, the order of the finalized sequence of codes may be used in later processes such as billing, to determine the principal diagnosis, etc. Exemplary screen 700' also includes fields for "present on admission" (POA) indicators, which provide information on whether each diagnosis was present when the patient was admitted to the hospital, or was acquired during the hospital stay. This information may be required documentation in some circumstances, and in some embodiments may be used for review and/or training purposes. In some embodiments, POA indicators may be automatically suggested, e.g., using the CLU system; while in other embodiments, POA indicators may only be input manually.

As discussed in connection with FIGS. 7A-7F, the user/customer may change the medical code sequence by re-ordering the codes, adding or deleting codes and/or changing the links and evidence supporting the codes. When the user is satisfied with the finalized sequence of codes, exemplary screen 700' provides a button for the codes to be saved, at which the coding process for the patient encounter becomes complete. In some embodiments, the CAC system may compare the finalized sequence of codes with stored coding rules, and may present the user with any applicable error or warning notifications prior to saving. As discussed above, once saved, the finalized sequence of codes may be sent to other processes such as billing and quality review.

As also discussed above, the finalized sequence of medical codes may be used for further training of the sequencing engine and/or the NLU engine of a CLU system. In particular, the finalized sequence of medical codes may be provided as feedback to adapt the sequencing engine and/or NLU engine accordingly. It should be appreciated that each user, customer and/or institution may have a corresponding sequencing engine or instance of a sequencing engine that continues to be adapted based on the feedback from that particular user, customer and/or institution. In particular, a given sequencing engine will propose a sequence of medical codes for a corresponding patient encounter and present the sequence to the corresponding user/customer, who may (but may not) then reorder the sequence or otherwise edit the sequence. Any changes to the sequence (e.g., reordering of the medical codes, deletion and/or addition of medical codes, etc.) may be used as feedback to further train the sequencing engine and/or the NLU engine. In this way, each sequencing engine or instance of a sequencing engine can learn the preferences, sequencing characteristics and behavior of the particular user, customer and/or institution to improve the respective performance from the customer perspective.

According to some embodiments, exemplary CAC GUI 700 may provide functionality to allow the user to edit a medical billing code sequence without removing the user from the CAC workspace to a separate screen (e.g., screen 700' illustrated FIG. 7G). FIG. 9A, for instance, illustrates an exemplary embodiment in which GUI 700 is extended to include editable POA fields (on the right-hand side of code list panel 730) and editable code sequencing fields (on the left-hand side of panel 730) for the set of billing codes under consideration for the patient encounter. In the example shown in FIG. 9A, the numerals 1 through 8 on the left-hand side of panel 730 indicate the current sequence of the user-approved codes (e.g., the sequence determined by sequencing engine 850), with the numeral 1 indicating that "Acute Respiratory Failure" (ICD-9-CM code 518.81) is the principal diagnosis, the numeral 2 indicating that "Thrombocytopenia NOS" (ICD-9-CM code 287.5) is the next secondary diagnosis, etc. ("Cirrhosis of Liver w/o Alcohol" (ICD-9-CM code 571.5) is a rejected code, and therefore does not receive a numeral in the sequence of user-approved codes for the patient encounter.) The sequence in which the user-approved billing codes for the patient encounter are finalized may be significant in determining the level of reimbursement for the patient encounter, e.g., by determining the diagnosis related group (DRG) of the patient encounter.

In some embodiments, as illustrated in FIG. 9A, CAC GUI 700 may provide further functionality in displaying the DRG determined by the current set of user-approved codes and their sequence (as well as any other relevant data, such as the POA data, patient demographic data, etc.) for the patient encounter. For example, exemplary GUI 700 in FIG. 9A includes a panel 760 in which the current DRG is displayed. In some embodiments, the CAC system may automatically correlate the current set of user-approved billing codes to the appropriate DRG to provide this display. This may be done, for example, using a stored set of DRG rules. In the example in FIG. 9A, the fact that code 518.81 for "Acute Respiratory Failure" has been placed first in the code sequence and therefore designated the principal diagnosis for the patient encounter gives rise to a DRG for the patient encounter of 189 ("Pulmonary Edema & Respiratory Failure").

In some embodiments, CAC GUI 700 may allow the user to change the sequencing of the set of user-approved billing codes before finalizing them. This may be done in any suitable way. For instance, FIG. 9B illustrates an example in which the numerals at the left-hand side of code list panel 730 are editable to change the code sequence. In this example, the user has changed the sequence number of code 482.1 ("Pneumonia due to *Pseudomonas*") to 1, indicating that this is the principal diagnosis. In this example, the CAC system has then automatically renumbered the rest of the user-approved codes to follow in sequence behind that principal diagnosis. Although not done in this example, in another example the codes could be reorganized within panel 730 such that the principal diagnosis (corresponding to numeral 1) always appears at the top of the panel, followed underneath by each successive numbered code in sequence, with non-approved (unnumbered) codes at the bottom of the panel, etc. In another example, the user input to modify the sequence of the user-approved codes may be in the form of dragging the codes to change their physical order within panel 730 (e.g., dragging a code to the top of the panel to make it the principal diagnosis), in response to which the CAC system may automatically renumber the codes accordingly. It should be appreciated that embodiments are not limited to any particular form of user input to modify the sequence of user-accepted codes for a patient encounter.

In some embodiments, in response to a user's modification of the sequence of user-approved billing codes for the current patient encounter, the CAC system may automatically update the DRG based on the modified sequence of user-approved codes, and may display the updated DRG in the GUI. FIG. 9B shows the example in which the user has changed the principal diagnosis from code 518.81 ("Acute Respiratory Failure") to code 482.1 ("Pneumonia due to *Pseudomonas*"). In response, the automatically determined DRG displayed in panel 760 has been updated from DRG 189 ("Pulmonary Edema & Respiratory Failure") to DRG 193 ("Simple Pneumonia & Pleurisy w MCC"). The fact that acute respiratory failure is the second diagnosis in the sequence and was not present on admission indicates that there was a major complication ("MCC") to the principal diagnosis of pneumonia, leading to this specific updated DRG. In some embodiments (not shown in FIG. 9B), GUI 700 may also display information indicating the level of reimbursement associated with the currently applicable DRG, allowing the coder to appreciate how individual modifications to the code set and sequence for the patient encounter may affect the reimbursement level. Some embodiments may provide an option for the CAC system to automatically determine the best sequencing for the current set of user-approved billing codes to result in the most appropriate DRG for the patient encounter. For example, in some embodiments, an automatic code sequencing feature may sequence codes such that any codes that would have an effect on the DRG are placed close enough to the top of the sequence (i.e., close enough to code #1, the principal diagnosis) for their effect on the DRG to be realized. In another example, some embodiments of an automatic code sequencing feature may sequence codes such that complication and major complication codes are placed close to the top of the sequence.

In some embodiments, in response to user input that changes the set of user-approved billing codes for the patient encounter by approving or removing approval of an engine-suggested code via the GUI, the CAC system may likewise automatically update the DRG based on the changed set of user-approved billing codes and display the updated DRG in the GUI. FIG. 9C shows an example in which the user, proceeding from the screen shown in FIG. 9B, has now removed approval of code 518.81 ("Acute Respiratory Failure") by changing that code's status from "accepted" back to merely "engine-suggested." In response, the remaining user-approved codes that were lower in the sequence than code 518.81 (which was previously second in the sequence) have now been renumbered, and code 518.81 is no longer part of the sequence. Also, the CAC system has updated the DRG displayed in panel 760 from DRG 193 ("Simple Pneumonia & Pleurisy w MCC") to DRG 195 ("Simple Pneumonia & Pleurisy w/o CC/MCC"), since there is now no code for a complication or major complication of the pneumonia appearing in the user-approved code set for the patient encounter. In some embodiments, such immediate updating of the automatically determined and displayed DRG may allow the user to better appreciate the immediate effects on reimbursement level as the user reviews and acts on engine-suggested codes (e.g., by accepting, rejecting, replacing, ignoring, etc.).

As discussed above, any changes by the user to the ordered sequence suggested by CAC application '875 (e.g., via sequencing engine 850) made via CAC interface 877 (e.g., using any of the techniques described herein) may be captured as feedback 895 and used to further train the sequencing engine 850. Accordingly, sequencing engine 850 may be improved during use and adapted to the preferences and coding behavior of individual customers.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

As an example, an illustrative implementation of a computer system 600 that may be used in connection with some implementations of a CAC system is shown in FIG. 6. One or more computer systems such as computer system 600 may be used to implement any of the functionality of the CAC system described above. As shown, the computer system 600 may include one or more processors 610 and one or more tangible, non-transitory computer-readable storage media (e.g., volatile storage 620 and one or more non-volatile storage media 630, which may be formed of any suitable non-volatile data storage media). The processor 610 may control writing data to and reading data from the volatile storage 620 and the non-volatile storage media 630 in any suitable manner, as the aspects of the present invention are not limited in this respect. To perform any of the functionality described herein, the processor 610 may execute one or more instructions stored in one or more computer-readable storage media (e.g., volatile storage 620), which may serve as tangible, non-transitory computer-readable storage media storing instructions for execution by the processor 610.

The phraseology and terminology used herein is for the purpose of description and should not be regarded as limiting. The use of "including," "comprising," "having," "containing", "involving", and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A system for automatically processing text comprising information regarding a patient encounter to prioritize medical billing codes derived from the text, the system comprising:

at least one storage medium storing processor-executable instructions; and at least one processor configured to execute the processor-executable instructions to:

generate an initial ordered sequence of a plurality of medical billing codes at least in part by:

analyzing the text to extract a plurality of facts from the text; and assigning the plurality of medical billing codes to the plurality of facts;

generate a revised ordered sequence of the plurality of medical billing codes by using a model trained at least in part on feedback from a user, wherein generating the revised ordered sequence comprises using the model to change the initial ordered sequence of the plurality of medical billing codes, the revised ordered sequence comprising a sequence beginning with a primary medical billing code corresponding to a primary diagnosis associated with the text; and output for presentation, in a user interface, the plurality of medical billing codes in the revised ordered sequence for review.

2. The system of claim 1, wherein the model is configured to provide a likelihood that a corresponding medical billing code is within a predetermined portion of the revised ordered sequence.

3. The system of claim 2, wherein the model is configured to provide a likelihood that the corresponding medical billing code is within a top half of the revised ordered sequence of the plurality of medical billing codes.

4. The system of claim 2, wherein the model is configured to provide a likelihood that the corresponding medical billing code is first in the revised ordered sequence of the plurality of medical billing codes.

5. The system of claim 1, wherein the model is configured to provide a likelihood that each medical billing code corresponds to the primary medical billing code corresponding to the principal diagnosis.

6. The system of claim 1, wherein the model is configured to provide a likelihood that each medical billing code corresponds to a secondary diagnosis.

7. The system of claim 1, wherein the model is trained using training data from which a plurality of features are extracted.

8. The system of claim 7, wherein the plurality of features includes at least one feature indicating a section from which a corresponding medical billing code was derived.

9. The system of claim 8, wherein the plurality of features includes at least one feature indicating a position within the section from which the corresponding medical billing code was derived.

10. The system of claim 9, wherein the at least one feature indicating the position indicates whether the corresponding medical billing code was extracted from a beginning, middle or end of the section from which the corresponding medical billing code was derived.

11. The system of claim 7, wherein the plurality of features includes at least one feature indicating whether a corresponding medical billing code is in a major complications list.

12. The system of claim 7, wherein the plurality of features includes at least one feature indicating whether a corresponding medical billing code is in a comorbidity list.

13. The system of claim 7, wherein the plurality of features includes at least one feature indicating whether a corresponding medical billing code is in a principal diagnosis list.

14. The system of claim 7, wherein the plurality of features includes at least one feature indicating historical information about a corresponding medical billing code.

15. The system of claim 14, wherein the historical information comprises a frequency of which the corresponding medical billing code was the primary medical billing code in the past.

16. The system of claim 7, wherein the plurality of features includes at least one feature indicating a type of document from which a corresponding medical billing code was derived.

17. The system of claim 7, wherein the plurality of features includes at least one feature indicating whether a corresponding medical billing code is one of a co-occurrence pair.

18. The system of claim 1, wherein the at least one processor is configured to execute the processor-executable instructions to receive the feedback from the user, the feedback indicating that the revised ordered sequence of the plurality of medical billing codes was modified, and wherein the at least one processor is configured to execute the processor-executable instructions to further train the model based at least in part on the feedback.

19. At least one non-transitory computer readable medium storing instructions that, when executed by at least one processor, perform a method for automatically processing text comprising information regarding a patient encounter to assign a sequence to medical billing codes derived from the text, the method comprising:
   generating an initial ordered sequence of a plurality of medical billing codes at least in part by:
      analyzing the text to extract a plurality of facts from the text; and
      assigning a plurality of medical billing codes to the plurality of facts;
   generating a revised ordered sequence of the plurality of medical billing codes by using a model trained at least in part on feedback from a user, wherein generating the revised ordered sequence comprises using the model to change the initial ordered sequence of the plurality of medical billing codes, the revised ordered sequence comprising a sequence beginning with a first medical billing code corresponding to a primary diagnosis associated with the text; and
   outputting for presentation, in a user interface, the plurality of medical billing codes in the revised ordered sequence for review.

20. A method for automatically processing text comprising information regarding a patient encounter to assign a sequence to medical billing codes derived from the text, the method comprising:
   generating an initial ordered sequence of a plurality of medical billing codes at least in part by:
      analyzing, by at least one processor, the text to extract a plurality of facts from the text; and
      assigning, by the at least one processor, a plurality of medical billing codes to the plurality of facts;
   generating a revised ordered sequence of the plurality of medical billing codes by using a model trained at least in part on feedback from a user, wherein generating the revised ordered sequence comprises using the model to change the initial ordered sequence of the plurality of medical billing codes, the revised ordered sequence comprising a sequence beginning with a first medical billing code corresponding to a primary diagnosis associated with the text; and
   outputting for presentation, in a user interface, the plurality of medical billing codes in the revised ordered sequence for review.

* * * * *